(12) United States Patent
Kozlowski et al.

(10) Patent No.: US 9,828,365 B2
(45) Date of Patent: Nov. 28, 2017

(54) FUSED TETRACYCLIC HETEROCYCLIC COMPOUNDS AND METHODS OF USE THEREOF FOR THE TREATMENT OF VIRAL DISEASES

(71) Applicants: MERCK SHARP & DOHME CORP., Rahway, NJ (US); Joseph Kozlowski, Rahway, NJ (US); Craig Coburn, San Rafael, CA (US); Wensheng Yu, Rahway, NJ (US); Ling Tong, Rahway, NJ (US); Bin Hu, Shanghai (CN); Bin Zhong, Shanghai (CN); Jinglai Hao, Shanghai (CN); Dahai Wang, Shanghai (CN); Tao Ji, Shanghai (CN)

(72) Inventors: Joseph Kozlowski, Princeton, NJ (US); Craig Coburn, Novato, CA (US); Wensheng Yu, Edison, NJ (US); Ling Tong, Warren, NJ (US); Bin Hu, Shanghai (CN); Bin Zhong, Shanghai (CN); Jinglai Hao, Shanghai (CN); Dahai Wang, Shanghai (CN); Tao Ji, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/104,584

(22) PCT Filed: Dec. 15, 2014

(86) PCT No.: PCT/US2014/070241
§ 371 (c)(1),
(2) Date: Jun. 15, 2016

(87) PCT Pub. No.: WO2015/094998
PCT Pub. Date: Jun. 25, 2015

(65) Prior Publication Data
US 2017/0217940 A1    Aug. 3, 2017

(30) Foreign Application Priority Data

Dec. 20, 2013  (WO) ................ PCT/CN2013/090030

(51) Int. Cl.
| | | |
|---|---|---|
| C07D 493/04 | (2006.01) | |
| C07D 405/14 | (2006.01) | |
| A61K 45/06 | (2006.01) | |
| A61K 31/4985 | (2006.01) | |
| A61K 31/7072 | (2006.01) | |
| A61K 31/4178 | (2006.01) | |

(52) U.S. Cl.
CPC ........ C07D 405/14 (2013.01); A61K 31/4178 (2013.01); A61K 31/4985 (2013.01); A61K 31/7072 (2013.01); A61K 45/06 (2013.01); C07D 493/04 (2013.01)

(58) Field of Classification Search
CPC .................................................... C07D 493/04
See application file for complete search history.

(56) References Cited

U.S. PATENT DOCUMENTS

| | | |
|---|---|---|
| 2003/0216463 A1 | 11/2003 | Kanojia et al. |
| 2004/0259915 A1 | 12/2004 | Kanojia et al. |
| 2006/0276511 A1 | 12/2006 | Serrano-Wu et al. |
| 2008/0044379 A1 | 2/2008 | Bachand et al. |
| 2008/0044380 A1 | 2/2008 | Bachand et al. |
| 2008/0050336 A1 | 2/2008 | Bachand et al. |
| 2008/0311075 A1 | 12/2008 | Bachand et al. |
| 2009/0020478 A1 | 1/2009 | Erwe et al. |
| 2009/0081636 A1 | 3/2009 | Huang et al. |
| 2009/0202483 A1 | 8/2009 | Bachand et al. |
| 2010/0041617 A1 | 2/2010 | Trepel et al. |

FOREIGN PATENT DOCUMENTS

| | | |
|---|---|---|
| WO | WO2010065668 | 6/2010 |
| WO | WO2010065674 | 6/2010 |

(Continued)

OTHER PUBLICATIONS

Tong et al., Alternative core development around the tetracyclic indole class of HCV NS5A inhibitors, Bioorganic & Medicinal Chemistry Letters, 2016, pp. 5132-5137, vol. 26, No. 20.

*Primary Examiner* — Laura L. Stockton
(74) *Attorney, Agent, or Firm* — Alysia A. Finnegan; Gloria M. Fuentes

(57) ABSTRACT

The present invention relates to novel Fused Tetracyclic Heterocyclic Compounds of Formula I: (I), wherein A, A', $R^{2A}$, $R^{2B}$, $R^7$, $R^8$, $R^9$, and $R^{10}$ are defined herein. The compounds and their pharmaceutically acceptable salts are useful for the prophylaxis or treatment of infection by HCV and the prophylaxis, treatment, or delay in the onset of disease caused by HCV. The present invention also relates to pharmaceutical compositions comprising at least one Fused Tetracyclic Heterocyclic Compound, optionally in combination with other antivirals, immunomodulators, antibiotics or vaccines, and methods of using the Fused Tetracyclic Heterocyclic Compounds for treating or preventing HCV infection in a patient.

(I)

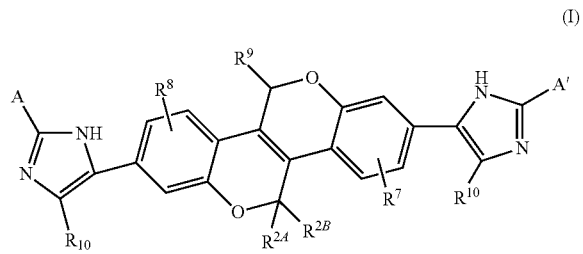

21 Claims, No Drawings

(56) References Cited

FOREIGN PATENT DOCUMENTS

| WO | WO2010065681 | | 6/2010 |
|---|---|---|---|
| WO | WO2010111483 | | 9/2010 |
| WO | 2012040924 | A1 | 4/2012 |
| WO | 2012041227 | A1 | 4/2012 |
| WO | WO -2012/040924 | A1 * | 4/2012 |
| WO | WO -2012/041227 | A1 * | 4/2012 |
| WO | WO2012040923 | | 4/2012 |
| WO | WO2012041014 | A1 | 4/2012 |
| WO | WO2012068234 | | 5/2012 |
| WO | 2015089810 | A1 | 6/2015 |

* cited by examiner

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:

<223> OTHER INFORMATION: Oligonucleotide Primer

<400> SEQUENCE: 1
ccggctacct gcccattc                                                18

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 2
ccagatcatc ctgatcgaca ag                                           22

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 3
acatcgcatc gagcgagcac gtac                                         24

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide Probe

<400> SEQUENCE: 4
cgcgtctcct ttgagctgtt tgca                                         24

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 5
acggcgagcc cttgg                                                   15

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 6
tttctgctgt ctttgggacc t                                            21

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 7

```
atggacaggc gccctga                                                17

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 8
ttgatgggca gcttggtttc                                             20

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide Probe

<400> SEQUENCE: 9
cacgccatgc gctgcgg                                                17

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 10
tgcggaaccg gtgagtaca                                              19

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 11
gcgggtttat ccaagaaagg a                                           21

<210> SEQ ID NO 12
<211> LENGTH: 21
<212> TYPE: DNA
<213> ORGANISM: Artificial Sequence
<220> FEATURE:
<223> OTHER INFORMATION: Oligoucleotide Probe

<400> SEQUENCE: 12
cggaattgcc aggacgaccg g                                           21
```

FUSED TETRACYCLIC HETEROCYCLIC COMPOUNDS AND METHODS OF USE THEREOF FOR THE TREATMENT OF VIRAL DISEASES

FIELD OF THE INVENTION

The present invention relates to Fused Tetracyclic Heterocyclic Compounds comprising 5,11-dihydrochromeno[4,3-c]chromene tetracyclic cores, compositions comprising at least one Fused Tetracyclic Heterocyclic Compound, and methods of using the Fused Tetracyclic Heterocyclic Compounds for treating or preventing HCV infection in a patient.

CROSS-REFERENCE TO RELATED APPLICATIONS

This application is a §371 National Phase Application of International Application No. PCT/US2014/070241, filed Dec. 15, 2014, which claims the benefit of Application No. PCT/CN2013/090030, filed Dec. 20, 2013, the contents of which are hereby incorporated by reference in their entirety.

REFERENCE TO SEQUENCE LISTING SUBMITTED ELECTRONICALLY

The sequence listing of the present application is submitted electronically via EFS-Web as an ASCII formatted sequence listing with a file name "23654USPCT-SEQLIST-26SEPT2016.TXT," creation date of Sep. 26, 2016, and a size of 2.80 KB. This sequence listing submitted EFS-Web is part of the specification and is herein incorporated by reference in its entirety.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are over 3 million chronically infected people in the United States alone, according to the U.S. Center for Disease Control. About 150 million individuals are chronically infected worldwide, with at least 3 to 4 million people being infected each year. Hepatitis C Fact Sheet, World Health Organization, July 2012. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, or sexually and vertically from infected mothers or carrier mothers to their off-spring.

Different approaches to HCV therapy have been taken, which include the inhibition of viral serine proteinase (NS3 protease), helicase, and RNA-dependent RNA polymerase (NS5B), and the development of a vaccine. Current and investigational treatments for HCV infection are reviewed in Poordad et al., Treating hepatitis C: current standard of care and emerging direct-acting antiviral agents. *Journal of Viral Hepatitis* 19: 449-464 (2012); and G. J. Dore, The changing therapeutic landscape for hepatitis C. *Med. J. Australia* 196: 629-632 (2012). Despite the availability of therapeutic treatment options, chronic HCV infection remains a major healthcare concern. Moreover, there is no established vaccine for HCV. Consequently, there is a need for improved therapeutic agents that effectively combat chronic HCV infection.

The HCV virion is an enveloped positive-strand RNA virus with a single oligoribonucleotide genomic sequence of about 9400 bases which encodes a polyprotein of about 3,000 amino acids. The protein products of the HCV gene consist of the structural proteins C, E1, and E2, and the non-structural proteins NS2, NS3, NS4A, NS4B, NS5A and NS5B. The nonstructural (NS) proteins are believed to provide the catalytic machinery for viral replication.

HCV NS5A is a 447 amino acid phosphoprotein which lacks a defined enzymatic function. The NS5A protein is either 56 kd or 58 kd, depending on its phosphorylation state (Tanji, et al. *J. Virol.* 69:3980-3986 (1995)). HCV NS5A resides in a replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065674.

Other HCV NS5A inhibitors and their use for reducing viral load in HCV infected humans have been described in U.S. Patent Publication No. US20060276511.

SUMMARY OF THE INVENTION

In one aspect, the present invention provides compounds having the formula (I):

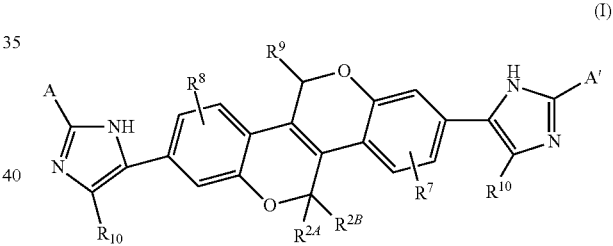

or a pharmaceutically acceptable salt thereof, wherein:

A is:

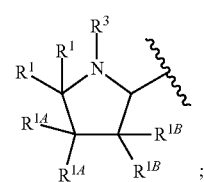

A' is:

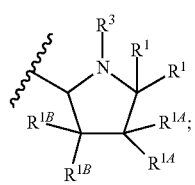

each occurrence of $R^1$ is independently selected from H, $C_1$-$C_6$ alkyl, $C_1$-$C_6$ haloalkyl and halo;

each occurrence of $R^{1A}$ is independently selected from H, $C_1$-$C_6$ alkyl, $C_1$-$C_6$ haloalkyl and halo, or one $R^{1A}$ group and an $R^1$ group that are attached to same ring, together with the ring carbon atoms to which they are attached, can combine to form a fused $C_3$-$C_7$ cycloalkyl group, or two $R^{1A}$ groups that are attached to the same carbon atom, and the common carbon atom to which they are attached, can combine to form a spirocyclic $C_3$-$C_7$ cycloalkyl group;

each occurrence of $R^{1B}$ is independently H, $C_1$-$C_6$ alkyl, $C_1$-$C_6$ haloalkyl or halo, or an $R^{1B}$ group and an $R^{1A}$ group that are attached to the same ring, together with the carbon atoms to which they are attached, can combine to form a fused $C_3$-$C_7$ cycloalkyl group, or an $R^{1B}$ group and an $R^1$ group that are attached to the same ring, can combine to form a bridging group having the formula —$CH_2$— or —$CH_2CH_2$—;

$R^{2A}$ is H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, 6 to 10-membered bicyclic heterocycloalkyl, $C_6$-$C_{10}$ aryl, or —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said 6 to 10-membered bicyclic heterocycloalkyl, or said $C_6$-$C_{10}$ aryl group, can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);

$R^{2B}$ is H; or alternatively, $R^{2A}$ and $R^{2B}$, together with the common carbon atom to which they are attached, form a carbonyl group;

each occurrence of $R^3$ is independently —C(O)—C($R^4$)$_2$NHC(O)O—$R^5$, —C(O)O—$R^5$; or —C(O)—C($R^4$)$_2$NR$^{11}$R$^{12}$;

each occurrence of $R^4$ is independently selected from H, $C_1$-$C_6$ alkyl, $C_1$-$C_6$ haloalkyl, $C_6$-$C_{10}$ aryl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group, said $C_6$-$C_{10}$ aryl group and said $C_3$-$C_7$ cycloalkyl group can be optionally substituted with up to 5 groups, each independently selected from halo, —CN, $C_1$-$C_6$ alkyl, $C_1$-$C_6$ haloalkyl, $C_3$-$C_7$ cycloalkyl, —O—$C_1$-$C_6$ alkyl, —N($R^6$)$_2$ and —O—($C_1$-$C_6$ haloalkyl), and wherein said $C_3$-$C_7$ cycloalkyl group can be optionally fused to a 4 to 6-membered monocyclic heterocycloalkyl group, and wherein said 4 to 8-membered monocyclic heterocycloalkyl group and said $C_3$-$C_7$ cycloalkyl group can be substituted on a ring carbon atom with a spirocyclic $C_3$-$C_6$ cycloalkyl group; and wherein said $C_3$-$C_7$ cycloalkyl group can be substituted on a ring carbon atom with a spirocyclic 3 to 6-membered monocyclic heterocycloalkyl group, and wherein two $R^4$ groups, that are attached to a common carbon atom, together with the common carbon atom to which they are attached, can join to form a $C_3$-$C_7$ cycloalkyl group;

each occurrence of $R^5$ is independently selected from $C_1$-$C_6$ alkyl, $C_3$-$C_7$ cycloalkyl and $C_6$-$C_{10}$ aryl;

each occurrence of $R^6$ is independently selected from H, $C_1$-$C_6$ alkyl and $C_3$-$C_7$ cycloalkyl;

$R^7$ and $R^8$ each represent up to 2 substituents, each independently selected from H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered heteroaryl, $C_6$-$C_{10}$ aryl, phenyl and —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said $C_6$-$C_{10}$ aryl group, or said phenyl group can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);

$R^9$ is H, $C_1$-$C_6$ alkyl, $C_3$-$C_7$ cycloalkyl, phenyl or halo;

each occurrence of $R^{10}$ is independently H, $C_1$-$C_6$ alkyl, $C_3$-$C_7$ cycloalkyl, phenyl or halo;

each occurrence of $R^{11}$ is independently $C_1$-$C_6$ alkyl, $C_1$-$C_6$ haloalkyl, $C_3$-$C_7$ cycloalkyl, or phenyl;

each occurrence of $R^{12}$ is independently $C_1$-$C_6$ alkyl, $C_1$-$C_6$ haloalkyl, $C_3$-$C_7$ cycloalkyl, or phenyl; and each occurrence of m is independently 0 or 1.

The Compounds of Formula (I) (also referred to herein as the "Fused Tetracyclic Heterocyclic Compounds") and pharmaceutically acceptable salts thereof can be useful, for example, for inhibiting HCV viral replication or replicon activity, and/or for treating or preventing HCV infection in a patient. Without being bound by any specific theory, it is believed that the Fused Tetracyclic Heterocyclic Compounds inhibit HCV viral replication by inhibiting HCV NS5A.

The present invention also provides methods for treating or preventing HCV infection in a patient, comprising administering to the patient an effective amount of at least one Fused Tetracyclic Heterocyclic Compound.

The details of the invention are set forth in the accompanying detailed description set forth below.

Other embodiments, aspects and features of the present invention are either further described in or will be apparent from the ensuing description, examples and appended claims.

DETAILED DESCRIPTION OF THE INVENTION

The present invention relates to certain Fused Tetracyclic Heterocyclic Compounds, compositions comprising at least one Fused Tetracyclic Heterocyclic Compound, and methods of using the Fused Tetracyclic Heterocyclic Compounds for treating or preventing HCV infection in a patient or for inhibiting HCV viral replication or replicon activity.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of a Fused Tetracyclic Heterocyclic Compound and/or an additional therapeutic agent, or a composition thereof that is effective in producing the desired therapeutic, ameliorative, inhibitory or preventative effect (e.g. inhibition of HCV viral replication) when administered to a patient suffering from an HCV infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —CH($CH_3$)$CH_2CH_2$—, —CH($CH_3$)— and —$CH_2$CH($CH_3$)$CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

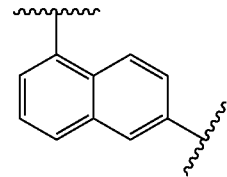

is understood to represent both:

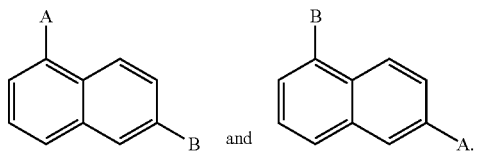

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

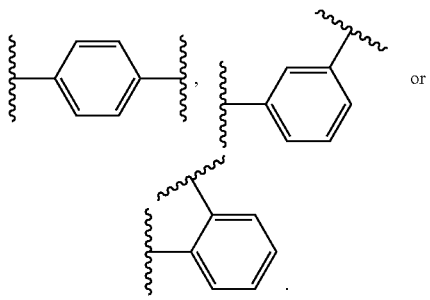

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

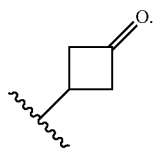 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 6-membered cycloalkenyl" refers to a cycloalkenyl group having from 4 to 6 ring carbon atoms. Unless otherwise indicated, a cycloalkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and had 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and either available bond on a heteroarylene ring can connect to either group flanking the heteroarylene group. For example, the group "A-heteroarylene-B," wherein the heteroarylene group is:

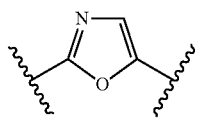 [SMILES: *c1cnc(*)o1]

is understood to represent both:

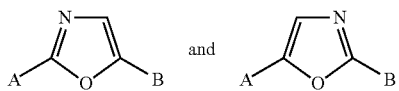

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. Unless otherwise indicated, a heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

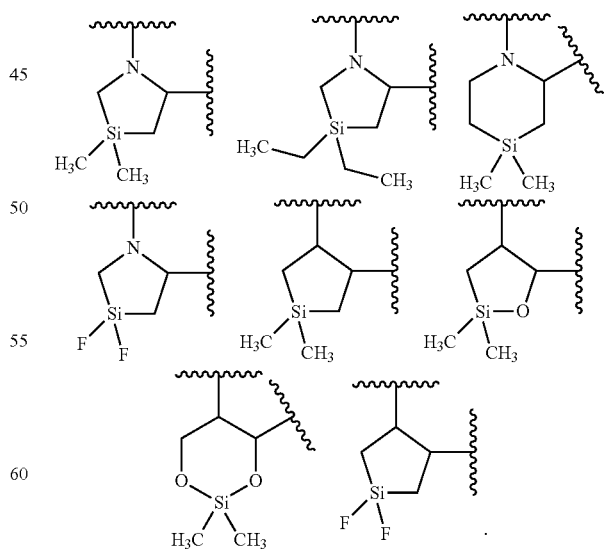

A ring carbon atom of a heterocycloalkyl group may be functionalized as a carbonyl group. An illustrative example of such a heterocycloalkyl group is:

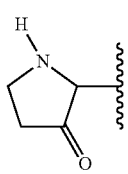

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 6 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 6-membered heterocycloalkenyl" refers to a heterocycloalkenyl group having 4, 5, or 6 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different. Examples of ring system substituents include alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), -(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

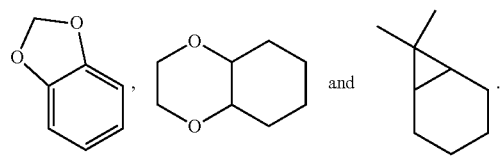

The term "silylalkyl," as used herein, refers to an alkyl group as defined above, wherein one or more of the alkyl group's hydrogen atoms has been replaced with a —Si(R$^x$)$_3$ group, wherein each occurrence of R$^x$ is independently C$_1$-C$_6$ alkyl, phenyl or a 3 to 6-membered cycloalkyl group. In one embodiment, a silylalkyl group has from 1 to 6 carbon atoms. In another embodiment, a silyl alkyl group contains a —Si(CH$_3$)$_3$ moiety. Non-limiting examples of silylalkyl groups include —CH$_2$—Si(CH$_3$)$_3$ and —CH$_2$CH$_2$—Si(CH$_3$)$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^6$, $R^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Fused Tetracyclic Heterocyclic Compound or a pharmaceutically acceptable salt or solvate of the compound. The transformation may occur by various mechanisms (e.g., by metabolic or chemical processes), such as, for example, through hydrolysis in blood.

For example, if a Fused Tetracyclic Heterocyclic Compound or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 6 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$ alkylcarbamoyl-$(C_1-C_2)$alkyl and piperidino-, pyrrolidino- or morpholino$(C_2-C_3)$alkyl, and the like.

Similarly, if a Fused Tetracyclic Heterocyclic Compound contains an alcohol functional group, a prodrug can be formed by the replacement of the hydrogen atom of the alcohol group with a group such as, for example, $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino $(C_1-C_4)$alkylene-aryl, arylacyl and α-aminoacyl, or α-aminoacyl-α-aminoacyl, where each α-aminoacyl group is independently selected from the naturally occurring L-amino acids, —$P(O)(OH)_2$, —$P(O)(O(C_1-C_6)alkyl)_2$ or glycosyl (the radical resulting from the removal of a hydroxyl group of the hemiacetal form of a carbohydrate), and the like.

If a Fused Tetracyclic Heterocyclic Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —$C(OH)C(O)OY^1$ wherein $Y^1$ is H, $(C_1-C_6)$ alkyl or benzyl, —$C(OY^2)Y^3$ wherein $Y^2$ is $(C_1-C_4)$ alkyl and $Y^3$ is $(C_1-C_6)$alkyl; carboxy $(C_1-C_6)$alkyl; amino$(C_1-C_4)$alkyl or mono-N— or di-N,N—$(C_1-C_6)$alkylaminoalkyl; —$C(Y^4)^5$ wherein $Y^4$ is H or methyl and $Y^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—$(C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Fused Tetracyclic Heterocyclic Compounds can form salts which are also within the scope of this invention. Reference to a Fused Tetracyclic Heterocyclic Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Fused Tetracyclic Heterocyclic Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Fused Tetracyclic Heterocyclic Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Fused Tetracyclic Heterocyclic Compounds may be atropisomers (e.g., substituted biaryls) and are considered as part of this invention. Enantiomers can also be directly separated using chiral chromatographic techniques.

It is also possible that the Fused Tetracyclic Heterocyclic Compounds may exist in different tautomeric forms, and all such forms are embraced within the scope of the invention. For example, all keto-enol and imine-enamine forms of the compounds are included in the invention.

Stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Fused Tetracyclic Heterocyclic Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt," "solvate," "ester," "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Fused Tetracyclic Heterocyclic Compounds, and of the salts, solvates, hydrates, esters and prodrugs of the Fused Tetracyclic Heterocyclic Compounds, are intended to be included in the present invention.

The following abbreviations are used below and have the following meanings: Ac is acyl; AcCl is acetyl chloride; AcOH or HOAc is acetic acid; Amphos is (4-(N,N)-dimethylaminophenyl)-di-tertbutylphosphine; Aq is aqueous; BF$_3$.OEt$_2$ is boron trifluoride etherate; BOC or Boc is tert-butyloxycarbonyl; BOP is Benzotriazole-1-yl-oxy-tris-(dimethylamino)-phosphonium hexafluorophosphate; n-BuLi is n-butyllithium; CBZ or Cbz is carbobenzoxy; DCM is dichloromethane; DIBALH is diisobutylaluminum hydride; DIEA is diisopropylethylamine (or Hunig's base); DMF is N,N-dimethylformamide; DMSO is dimethylsulfoxide; EtOAc is ethyl acetate; Et$_3$N or NEt$_3$ is triethylamine; HATU is O-(7-azabenzotriazol-1-yl)-N,N,N',N'-tetramethyluronium hexafluorophosphate; HPLC is high performance liquid chromatography; KOAc is potassium acetate; LCMS is liquid chromatography/mass spectrometry; MeI is iodomethane; MeOH is methanol; NBS is N-bromosuccinimide; $Pd_2(dba)_3$ is tris(dibenzylideneacetone) dipalladium; $PdCl_2(dppf)_2$ is [1,1'-Bis(diphenylphosphino) ferrocene]dichloro palladium(II); $PdCl_2(dppf)_2 \cdot CH_2Cl_2$ is [1,1'-Bis(diphenylphosphino)ferrocene]dichloro palladium(II) complex with dichloromethane; $PdCl_2(dppf)$ is 1,1'-bis(diphenylphosphino)ferrocene palladium dichloride; SFC is supercritical fluid chromatography; TBAF is tetrabutylammonium fluoride; TBDMSCl is tert-butyldimethylsilyl chloride; TEA is triethylamine, and THF is tetrahydrofuran.

The Compounds of Formula (I)

The present invention provides Fused Tetracyclic Heterocyclic Compounds of Formula (I):

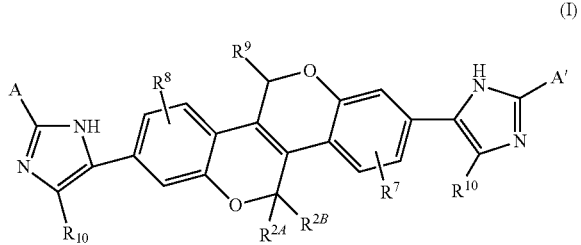

and pharmaceutically acceptable salts thereof, wherein:
A is:

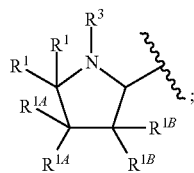

and
A' is:

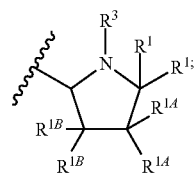

and wherein $R^{2A}$, $R^{2B}$, $R^7$, $R^8$, $R^9$, and $R^{10}$ are defined above for the Compounds of Formula (I).

A first embodiment of the invention (Embodiment E1) is a compound of Formula I, or a pharmaceutically acceptable salt thereof, wherein, within A or A' or within both A and A', each occurrence of $R^1$ is H; and wherein all other variables are as originally defined (i.e. as defined in Formula I in the Summary of the Invention).

A second embodiment (Embodiment E2) is a compound of Formula I, or a pharmaceutically acceptable salt thereof, wherein, within A or A' or within both A and A', one occurrence of $R^1$ is H and one occurrence of $R^1$ is $C_1$-$C_6$ alkyl, and all other variables are as defined in Embodiment E1.

A third embodiment (Embodiment E3) is a compound of Formula I, or a pharmaceutically acceptable salt thereof, wherein, within A or A' or within both A and A', one occurrence of $R^1$ is H and one occurrence of $R^1$ is $C_1$-$C_6$ haloalkyl, and all other variables are as defined in Embodiment E1.

A fourth embodiment (Embodiment E4) is a compound of Formula I, or a pharmaceutically acceptable salt thereof, wherein, within A or A' or within both A and A', one occurrence of $R^1$ is H and one occurrence of $R^1$ is halo, and all other variables are as defined in Embodiment E1.

A fifth embodiment (Embodiment E5) is a compound of Formula I, or a pharmaceutically acceptable salt thereof, wherein, within A or A' or within both A and A', one occurrence of $R^1$ is $C_1$-$C_6$ alkyl and one occurrence of $R^1$ is $C_1$-$C_6$ haloalkyl or halo; or both occurrences of $R^1$ are $C_1$-$C_6$ alkyl, and all other variables are as defined in Embodiment E1.

A sixth embodiment (Embodiment E6) is a compound of Formula I, or a pharmaceutically acceptable salt thereof, wherein, within A or A' or within both A and A', one occurrence of $R^1$ is $C_1$-$C_6$ haloalkyl and one occurrence of $R^1$ is halo, and all other variables are as defined in Embodiment E1.

A seventh embodiment (Embodiment E7) is a compound of Formula I, or a pharmaceutically acceptable salt thereof, wherein, within A or A' or within both A and A', both occurrences of $R^1$ are halo, or both occurrences of $R^1$ are $C_1$-$C_6$ haloalkyl, and all other variables are as defined in Embodiment E1.

An eighth embodiment (Embodiment E8) is a compound of Formula I, or a pharmaceutically acceptable salt thereof, wherein, within A or A' or within both A and A', $R^1$ is as defined in any of Embodiments E1-E7, each occurrence of $R^{1A}$ is H, and all other variables are as defined in Embodiment E1.

A ninth embodiment (Embodiment E9) is a compound of Formula I, or a pharmaceutically acceptable salt thereof, wherein, within A or A' or within both A and A', $R^1$ is as defined in any of Embodiments E1-E7, one occurrence of $R^{1A}$ is H, one occurrence of $R^{1A}$ is $C_1$-$C_6$ alkyl, and all other variables are as defined in Embodiment E1.

A tenth embodiment (Embodiment E10) is a compound of Formula I, or a pharmaceutically acceptable salt thereof, wherein, within A or A' or within both A and A', $R^1$ is as defined in any of Embodiments E1-E7, one occurrence of $R^{1A}$ is H, one occurrence of $R^{1A}$ is $C_1$-$C_6$ haloalkyl, and all other variables are as defined in Embodiment E1.

An eleventh embodiment (Embodiment E11) is a compound of Formula I, or a pharmaceutically acceptable salt thereof, wherein, within A or A' or within both A and A', $R^1$ is as defined in any of Embodiments E1-E7, one occurrence of $R^{1A}$ is H, one occurrence of $R^{1A}$ is halo, and all other variables are as defined in Embodiment E1.

An twelfth embodiment (Embodiment E12) is a compound of Formula I, or a pharmaceutically acceptable salt thereof, wherein, within A or A' or within both A and A', $R^1$ is as defined in any of Embodiments E1-E7, one occurrence of $R^{1A}$ is H, one occurrence of $R^{1A}$ is F, and all other variables are as defined in Embodiment E1.

A thirteenth embodiment (Embodiment E13) is a compound of Formula I, or a pharmaceutically acceptable salt thereof, wherein, within A or A' or within both A and A', $R^1$ is as defined in any of Embodiments E1-E7, one occurrence of $R^{1A}$ is $C_1$-$C_6$ alkyl, one occurrence of $R^{1A}$ is $C_1$-$C_6$ haloalkyl or halo, and all other variables are as defined in Embodiment E1.

A fourteenth embodiment (Embodiment E14) is a compound of Formula I, or a pharmaceutically acceptable salt thereof, wherein, within A or A' or within both A and A', $R^1$ is as defined in any of Embodiments E1-E7, one occurrence of $R^{1A}$ is $C_1$-$C_6$ alkyl, one occurrence of $R^{1A}$ is F, and all other variables are as defined in Embodiment E1.

A fifteenth embodiment (Embodiment E15) is a compound of Formula I, or a pharmaceutically acceptable salt thereof, wherein, within A or A' or within both A and A', $R^1$ is as defined in any of Embodiments E1-E7, both occurrences of $R^{1A}$ are $C_1$-$C_6$ alkyl, and all other variables are as defined in Embodiment E1.

A sixteenth embodiment (Embodiment E16) is a compound of Formula I, or a pharmaceutically acceptable salt thereof, wherein, within A or A' or within both A and A', $R^1$ is as defined in any of Embodiments E1-E7, one occurrence of $R^{1A}$ is $C_1$-$C_6$ haloalkyl, one occurrence of $R^{1A}$ is halo, and all other variables are as defined in Embodiment E1.

A seventeenth embodiment (Embodiment E17) is a compound of Formula I, or a pharmaceutically acceptable salt thereof, within A or A' or within both A and A', $R^1$ is as defined in any of Embodiments E1-E7, both occurrences of $R^{1A}$ are $C_1$-$C_6$ haloalkyl, and all other variables are as defined in Embodiment E1.

A eighteenth embodiment (Embodiment E18) is a compound of Formula I, or a pharmaceutically acceptable salt thereof, within A or A' or within both A and A', $R^1$ is as defined in any of Embodiments E1-E7, both occurrences of $R^{1A}$ are halo, and all other variables are as defined in Embodiment E1.

A nineteenth embodiment (Embodiment E19) is a compound of Formula I, or a pharmaceutically acceptable salt thereof, wherein, within A or A' or within both A and A', $R^1$ is as defined in any of Embodiments E1-E7, both occurrences of $R^{1A}$ are F, and all other variables are as defined in Embodiment E1.

A twentieth embodiment (Embodiment E20) is a compound of Formula I, or a pharmaceutically acceptable salt thereof, wherein, within A or A' or within both A and A', $R^1$ is as defined in any of Embodiments E1-E7, wherein two $R^{1A}$ groups that are attached to the same carbon atom, and the common carbon atom to which they are attached, combine to form a spirocyclic $C_3$-$C_7$ cycloalkyl group, and all other variables are as defined in Embodiment E1.

A twenty-first embodiment (Embodiment E21) is a compound of Formula I, or a pharmaceutically acceptable salt thereof, wherein, within A or A' or within both A and A', one occurrence of $R^1$ is as defined in any of Embodiments E1-E7, wherein one $R^{1A}$ group and an $R^1$ group that are attached to same ring, together with the ring carbon atoms to which they are attached, combine to form a fused $C_3$-$C_7$ cycloalkyl group, wherein one occurrence of $R^{1A}$ is H, and all other variables are as defined in Embodiment E1.

A twenty-second embodiment (Embodiment E22) is a compound of Formula I, or a pharmaceutically acceptable salt thereof, wherein, within A or A' or within both A and A', one occurrence of $R^1$ is as defined in any of Embodiments E1-E7, wherein one $R^{1A}$ group and an $R^1$ group that are attached to same ring, together with the ring carbon atoms to which they are attached, combine to form a fused $C_3$-$C_7$ cycloalkyl group, one occurrence of $R^{1A}$ is $C_1$-$C_6$ alkyl, $C_1$-$C_6$ haloalkyl or halo, and all other variables are as defined in Embodiment E1.

A twenty-third embodiment (Embodiment E23) is a compound of Formula I, or a pharmaceutically acceptable salt thereof, wherein, within A or A' or within both A and A', $R^1$ is as defined in any of Embodiments E1-E7, $R^{1A}$ is as defined in any of Embodiments E8-E20, or $R^1$ and $R^{1A}$ are as defined in Embodiment E21 or Embodiment E22, each occurrence of $R^{1B}$ is H, and all other variables are as defined in Embodiment E1.

A twenty-fourth embodiment (Embodiment E24) is a compound of Formula I, or a pharmaceutically acceptable salt thereof, wherein, within A or A' or within both A and A', $R^1$ is as defined in any of Embodiments E1-E7, $R^{1A}$ is as defined in any of Embodiments E8-E20, or $R^1$ and $R^{1A}$ are as defined in Embodiment E21 or Embodiment E22, one occurrence of $R^{1B}$ is H, one occurrence of $R^{1B}$ is $C_1$-$C_6$ alkyl and all other variables are as defined in Embodiment E1.

A twenty-fifth embodiment (Embodiment E25) is a compound of Formula I, or a pharmaceutically acceptable salt thereof, wherein, within A or A' or within both A and A', $R^1$ is as defined in any of Embodiments E1-E7, $R^{1A}$ is as defined in any of Embodiments E8-E20, or $R^1$ and $R^{1A}$ are as defined in Embodiment E21 or Embodiment E22, one occurrence of $R^{1B}$ is H, one occurrence of $R^{1B}$ is $C_1$-$C_6$ haloalkyl and all other variables are as defined in Embodiment E1.

A twenty-sixth embodiment (Embodiment E26) is a compound of Formula I, or a pharmaceutically acceptable salt thereof, wherein, within A or A' or within both A and A', $R^1$ is as defined in any of Embodiments E1-E7, $R^{1A}$ is as defined in any of Embodiments E8-E20, or $R^1$ and $R^{1A}$ are as defined in Embodiment E21 or Embodiment E22, one occurrence of $R^{1B}$ is H, one occurrence of $R^{1B}$ is halo and all other variables are as defined in Embodiment E1.

A twenty-seventh embodiment (Embodiment E27) is a compound of Formula I, or a pharmaceutically acceptable salt thereof, wherein, within A or A' or within both A and A', $R^1$ is as defined in any of Embodiments E1-E7, $R^{1A}$ is as defined in any of Embodiments E8-E20, or $R^1$ and $R^{1A}$ are as defined in Embodiment E21 or Embodiment E22, one occurrence of $R^{1B}$ is $C_1$-$C_6$ alkyl, one occurrence of $R^{1B}$ is $C_1$-$C_6$ haloalkyl or halo and all other variables are as defined in Embodiment E1

A twenty-eighth embodiment (Embodiment E28) is a compound of Formula I, or a pharmaceutically acceptable salt thereof, wherein, within A or A' or within both A and A', $R^1$ is as defined in any of Embodiments E1-E7, $R^{1A}$ is as defined in any of Embodiments E8-E20, or $R^1$ and $R^{1A}$ are as defined in Embodiment E21 or Embodiment E22, each occurrence of $R^{1B}$ is $C_1$-$C_6$ haloalkyl or each occurrence of $R^{1B}$ is halo and all other variables are as defined in Embodiment E1

A twenty-ninth embodiment (Embodiment E29) is a compound of Formula I, or a pharmaceutically acceptable salt thereof, wherein, within A or A' or within both A and A', $R^1$ is as defined in any of Embodiments E1-E7, $R^{1A}$ is as defined in any of Embodiments E8-E20, or $R^1$ and $R^{1A}$ are as defined in Embodiment E21 or Embodiment E22, one occurrence of $R^{1B}$ is $C_1$-$C_6$ haloalkyl and one occurrence of $R^{1B}$ is halo, and all other variables are as defined in Embodiment E1.

A thirtieth embodiment (Embodiment E30) is a compound of Formula I, or a pharmaceutically acceptable salt thereof, wherein, within A or A' or within both A and A', $R^1$ is as defined in any of Embodiments E1-E7, one occurrence of $R^{1A}$ is H, one $R^{1B}$ group and an $R^{1A}$ group that are attached to the same ring, together with the carbon atoms to which they are attached, combine to form a fused $C_3$-$C_7$ cycloalkyl group, one occurrence of $R^{1B}$ is H, and all other variables are as defined in Embodiment E1.

A thirty-first embodiment (Embodiment E31) is a compound of Formula I, or a pharmaceutically acceptable salt thereof, wherein, within A or A' or within both A and A', $R^1$ is as defined in any of Embodiments E1-E7, one occurrence of $R^{1A}$ is $C_1$-$C_6$ alkyl, $C_1$-$C_6$ haloalkyl, or halo, one $R^{1B}$ group and an $R^{1A}$ group that are attached to the same ring, together with the carbon atoms to which they are attached, combine to form a fused $C_3$-$C_7$ cycloalkyl group, one occurrence of $R^{1B}$ is H, and all other variables are as defined in Embodiment E1.

A thirty-second embodiment (Embodiment E32) is a compound of Formula I, or a pharmaceutically acceptable salt thereof, wherein, within A or A' or within both A and A', $R^1$ is as defined in any of Embodiments E1-E7, one occurrence of $R^{1A}$ is H, one $R^{1B}$ group and an $R^{1A}$ group that are attached to the same ring, together with the carbon atoms to which they are attached, combine to form a fused $C_3$-$C_7$ cycloalkyl group, one occurrence of $R^{1B}$ is $C_1$-$C_6$ alkyl, $C_1$-$C_6$ haloalkyl, or halo, and all other variables are as defined in Embodiment E1.

A thirty-third embodiment (Embodiment E33) is a compound of Formula I, or a pharmaceutically acceptable salt thereof, wherein, within A or A' or within both A and A', one occurrence of $R^1$ is H, $R^{1A}$ is as defined in any of Embodiments E8-E20, an $R^{1B}$ group and an $R^1$ group that are attached to the same ring, combine to form a bridging group having the formula —$CH_2$— or —$CH_2CH_2$—, one occurrence of $R^{1B}$ is H, and all other variables are as defined in Embodiment E1.

A thirty-fourth embodiment (Embodiment E34) is a compound of Formula I, or a pharmaceutically acceptable salt thereof, wherein, within A or A' or within both A and A', one occurrence of $R^1$ is $C_1$-$C_6$ alkyl, $C_1$-$C_6$ haloalkyl, or halo, $R^{1A}$ is as defined in any of Embodiments E8-E20, an $R^{1B}$ group and an $R^1$ group that are attached to the same ring, combine to form a bridging group having the formula —$CH_2$— or —$CH_2CH_2$—, one occurrence of $R^{1B}$ is H, and all other variables are as defined in Embodiment E1.

A thirty-fifth embodiment (Embodiment E35) is a compound of Formula I, or a pharmaceutically acceptable salt thereof, wherein, within A or A' or within both A and A', one occurrence of $R^1$ is H, $C_1$-$C_6$ alkyl, $C_1$-$C_6$ haloalkyl, or halo, $R^{1A}$ is as defined in any of Embodiments E8-E20, an $R^{1B}$ group and an $R^1$ group that are attached to the same ring, combine to form a bridging group having the formula —$CH_2$— or —$CH_2CH_2$—, one occurrence of $R^{1B}$ is H, $C_1$-$C_6$ alkyl, $C_1$-$C_6$ haloalkyl, or halo, and all other variables are as defined in Embodiment E1.

A thirty-sixth embodiment (Embodiment E36) is a compound of Formula I, or a pharmaceutically acceptable salt thereof, wherein, within A or A' or within both A and A', $R^1$, $R^{1A}$, and $R^{1B}$ are as defined in any of Embodiments E1-E35, $R^3$ is —C(O)—C($R^4$)$_2$NHC(O)—$R^5$, and all other variables are as defined in Embodiment E1.

A thirty-seventh embodiment (Embodiment E37) is a compound of Formula I, or a pharmaceutically acceptable salt thereof, wherein, within A or A' or within both A and A', $R^1$, $R^{1A}$, and $R^{1B}$ are as defined in any of Embodiments E1-E35, $R^3$ is —C(O)—C($R^4$)$_2$NR$^{11}$R$^{12}$, and all other variables are as defined in Embodiment E1.

A thirty-eight embodiment (Embodiment E38) is a compound of Formula I, or a pharmaceutically acceptable salt thereof, wherein, within A or A' or within both A and A', $R^1$, $R^{1A}$, and $R^{1B}$ are as defined in any of Embodiments E1-E35, $R^3$ is —C(O)O—$R^5$, and all other variables are as defined in Embodiment E1.

A thirty-ninth embodiment (Embodiment E39) is a compound of Formula I, or a pharmaceutically acceptable salt thereof, wherein, within A or A' or within both A and A', $R^1$, $R^{1A}$, and $R^{1B}$ are as defined in any of Embodiments E1-E35, $R^3$ is —C(O)O—C(CH$_3$)$_3$, and all other variables are as defined in Embodiment E1.

A fortieth embodiment (Embodiment E40) is a compound of Formula I, or a pharmaceutically acceptable salt thereof, wherein, within A or A' or within both A and A', $R^1$, $R^{1A}$, and $R^{1B}$ are as defined in any of Embodiments E1-E35, $R^3$ is:

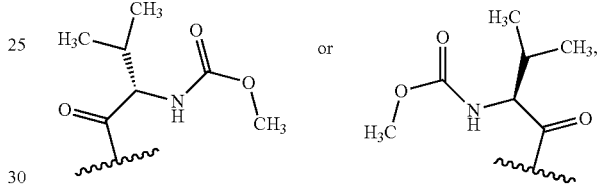

and all other variables are as defined in Embodiment E1.

A forty-first embodiment (Embodiment E41) is a compound of Formula I, or a pharmaceutically acceptable salt thereof, wherein, $R^1$, $R^{1A}$, $R^{1B}$ and $R^3$ are as defined in any of Embodiments E1-E40, $R^{2A}$ and $R^{2B}$, together with the common carbon atom to which they are attached, form a carbonyl group, and all other variables are as defined in Embodiment E1.

A forty-second embodiment (Embodiment E42) is a compound of Formula I, or a pharmaceutically acceptable salt thereof, wherein, $R^1$, $R^{1A}$, $R^{1B}$ and $R^3$ are as defined in any of Embodiments E1-E40, $R^{2A}$ and $R^{2B}$ are H, and all other variables are as defined in Embodiment E1.

A forty-third embodiment (Embodiment E43) is a compound of Formula I, or a pharmaceutically acceptable salt thereof, wherein, $R^1$, $R^{1A}$, $R^{1B}$ and $R^3$ are as defined in any of Embodiments E1-E40, $R^{2A}$ is $C_1$-$C_6$ alkyl, $R^{2B}$ is H, and all other variables are as defined in Embodiment E1.

A forty-fourth embodiment (Embodiment E44) is a compound of Formula I, or a pharmaceutically acceptable salt thereof, wherein, $R^1$, $R^{1A}$, $R^{1B}$ and $R^3$ are as defined in any of Embodiments E1-E40, $R^{2A}$ is $C_3$-$C_7$ cycloalkyl, wherein said $C_3$-$C_7$ cycloalkyl group is optionally substituted with up to 3 groups, which can be the same or different, and are selected from halo, —CN, $C_1$-$C_6$ alkyl, $C_1$-$C_6$ haloalkyl, —O— $C_1$-$C_6$ alkyl, —($C_1$-$C_6$ alkylene)-O— $C_1$-$C_6$ alkyl and —O—($C_1$-$C_6$ haloalkyl); $R^{2B}$ is H, and all other variables are as defined in Embodiment E1.

A forty-fifth embodiment (Embodiment E45) is a compound of Formula I, or a pharmaceutically acceptable salt thereof, wherein, $R^1$, $R^{1A}$, $R^{1B}$ and $R^3$ are as defined in any of Embodiments E1-E40, $R^{2A}$ is phenyl, wherein said phenyl group is optionally substituted with up to 3 groups, which can be the same or different, and are selected from halo, —CN, $C_1$-$C_6$ alkyl, $C_1$-$C_6$ haloalkyl, —O— $C_1$-$C_6$ alkyl, —(C$_1$-C$_6$ alkylene)-O— C$_1$-C$_6$ alkyl and —O—(C$_1$-C$_6$ haloalkyl); R$^{2B}$ is H, and all other variables are as defined in Embodiment E1.

A forty-sixth embodiment (Embodiment E46) is a compound of Formula I, or a pharmaceutically acceptable salt thereof, wherein, R$^1$, R$^{1A}$, R$^{1B}$ and R$^3$ are as defined in any of Embodiments E1-E40, R$^{2A}$ is phenyl, wherein said phenyl group is substituted with —O— C$_1$-C$_6$ alkyl, R$^{2B}$ is H, and all other variables are as defined in Embodiment E1.

A forty-seventh embodiment (Embodiment E47) is a compound of Formula I, or a pharmaceutically acceptable salt thereof, wherein, R$^1$, R$^{1A}$, R$^{1B}$ and R$^3$ are as defined in any of Embodiments E1-E40, R$^{2A}$ is halo, R$^{2B}$ is H, and all other variables are as defined in Embodiment E1.

A forty-eighth embodiment (Embodiment E48) is a compound of Formula I, or a pharmaceutically acceptable salt thereof, wherein, R$^1$, R$^{1A}$, R$^{1B}$ and R$^3$ are as defined in any of Embodiments E1-E40, R$^{2A}$ is C$_1$-C$_6$ haloalkyl, R$^{2B}$ is H, and all other variables are as defined in Embodiment E1.

A forty-ninth embodiment (Embodiment E49) is a compound of Formula I, or a pharmaceutically acceptable salt thereof, wherein, R$^1$, R$^{1A}$, R$^{1B}$ and R$^3$ are as defined in any of Embodiments E1-E40, R$^{2A}$ is methyl, R$^{2B}$ is H, and all other variables are as defined in Embodiment E1.

A fiftieth embodiment (Embodiment E50) is a compound of Formula I, or a pharmaceutically acceptable salt thereof, wherein, R$^1$, R$^{1A}$, R$^{1B}$ and R$^3$ are as defined in any of Embodiments E1-E40, R$^{2A}$ is cyclopropyl, R$^{2B}$ is H, and all other variables are as defined in Embodiment E1.

A fifty-first embodiment (Embodiment E51) is a compound of Formula I, or a pharmaceutically acceptable salt thereof, wherein, R$^1$, R$^{1A}$, R$^{1B}$ and R$^3$ are as defined in any of Embodiments E1-E40, R$^{2A}$ is thiazole, wherein said thiazole group can be optionally substituted with up to 2 groups, which can be the same or different, and are selected from halo, —CN, C$_1$-C$_6$ alkyl, C$_1$-C$_6$ haloalkyl, —O—C$_1$-C$_6$ alkyl, —(C$_1$-C$_6$ alkylene)-O— C$_1$-C$_6$ alkyl and —O—(C$_1$-C$_6$ haloalkyl); R$^{2B}$ is H, and all other variables are as defined in Embodiment E1.

A fifty-second embodiment (Embodiment E52) is a compound of Formula I, or a pharmaceutically acceptable salt thereof, wherein, R$^1$, R$^{1A}$, R$^{1B}$ and R$^3$ are as defined in any of Embodiments E1-E40, R$^{2A}$ is thiophene, wherein said thiophene group can be optionally substituted with up to 2 groups, which can be the same or different, and are selected from halo, —CN, C$_1$-C$_6$ alkyl, C$_1$-C$_6$ haloalkyl, —O—C$_1$-C$_6$ alkyl, —(C$_1$-C$_6$ alkylene)-O— C$_1$-C$_6$ alkyl and —O—(C$_1$-C$_6$ haloalkyl); R$^{2B}$ is H, and all other variables are as defined in Embodiment E1.

A fifty-third embodiment (Embodiment E53) is a compound of Formula I, or a pharmaceutically acceptable salt thereof, wherein A and A' are independently selected from:

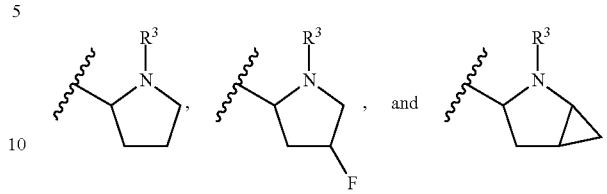

R$^3$ is as defined in any of embodiments E36-E40, R$^{2A}$ and R$^{2B}$ are as defined in any of Embodiments E41-E52, and all other variables are as defined in Embodiment E1.

A fifty-forth embodiment (Embodiment E54) is a compound of Formula IA:

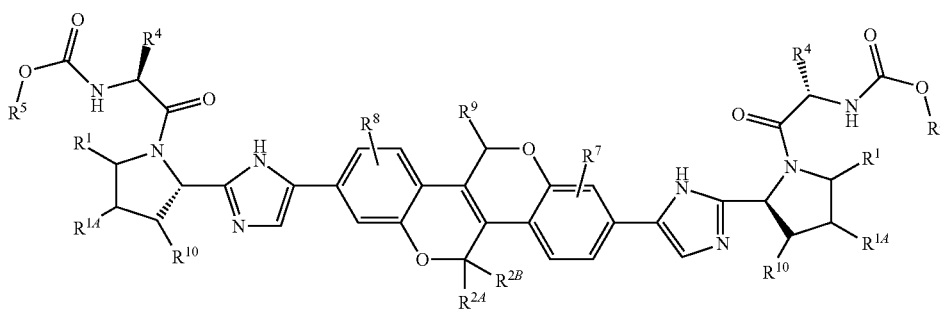

(IA)

or a pharmaceutically acceptable salt thereof, wherein:

R$^{2A}$ is H, C$_1$-C$_6$ alkyl, C$_3$-C$_7$ cycloalkyl, phenyl, thiophene, or thiazole, wherein said C$_3$-C$_7$ cycloalkyl group, said phenyl group, or said thiophene group can be optionally substituted with up to 3 groups, and said thiazole group can be optionally substituted with up to 2 groups, which can be the same or different, and are selected from halo, —CN, C$_1$-C$_6$ alkyl, C$_1$-C$_6$ haloalkyl, —O—C$_1$-C$_6$ alkyl, —(C$_1$-C$_6$ alkylene)-O—C$_1$-C$_6$ alkyl and —O—(C$_1$-C$_6$ haloalkyl); and R$^{2B}$ is H;

or alternatively, R$^{2A}$ and R$^{2B}$, together with the common carbon atom to which they are attached, form a carbonyl group;

R$^7$, R$^8$, R$^9$, and R$^{10}$ are as defined in Embodiment E1, each occurrence of R$^4$ is independently C$_1$-C$_6$ alkyl;

each occurrence of R$^5$ is independently C$_1$-C$_6$ alkyl;

R$^1$ is H, and each occurrence of R$^{1A}$ is independently selected from H or F.

A fifty-fifth embodiment (Embodiment E55) is a compound of Formula IA, wherein: R$^{2A}$, R$^{2B}$, R$^5$, R$^1$, and R$^{1A}$ are as defined in Embodiment E54, R$^7$, R$^8$, R$^9$, and R$^{10}$ are as defined in Embodiment E1, and at least one occurrences of R$^4$ is isopropyl.

A fifty-sixth embodiment (Embodiment E56) is a compound of Formula IA, wherein: R$^{2A}$, R$^{2B}$, R$^1$, R$^4$ and R$^{1A}$ are as defined in Embodiment E54, R$^7$, R$^8$, R$^9$, and R$^{10}$ are as defined in Embodiment E1, and R$^5$ is methyl.

A fifty-seventh embodiment of the invention (Embodiment E57), is a compound having the structure:

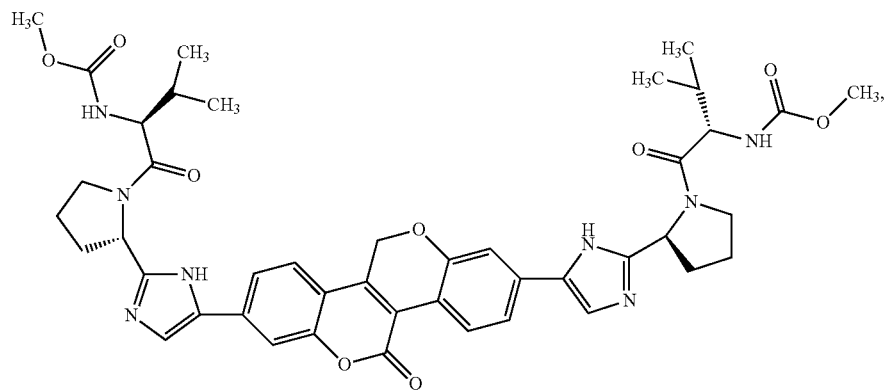
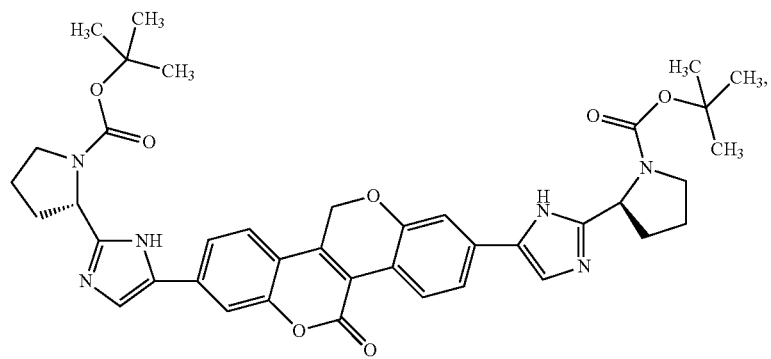
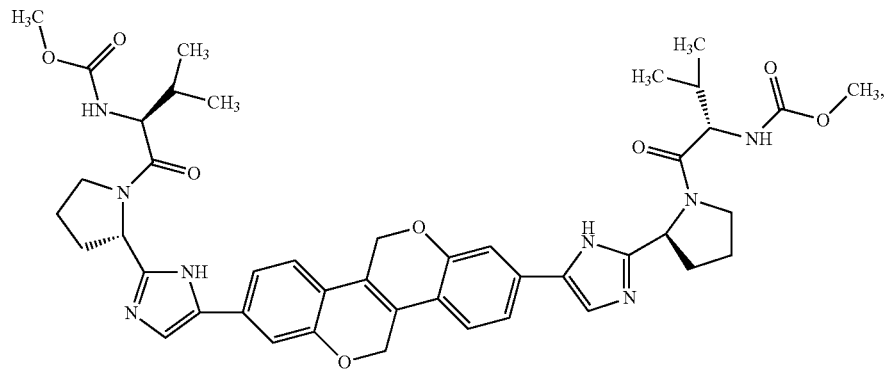
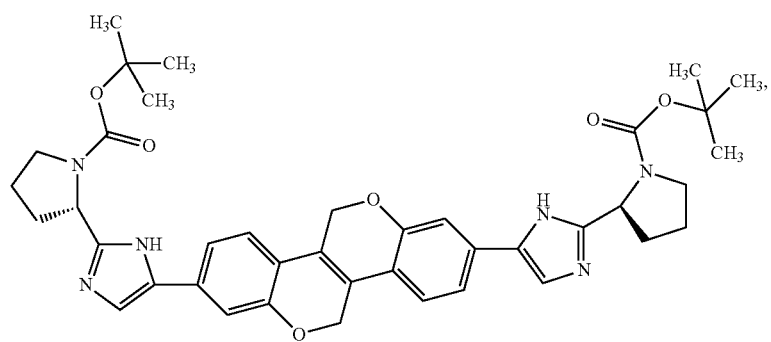

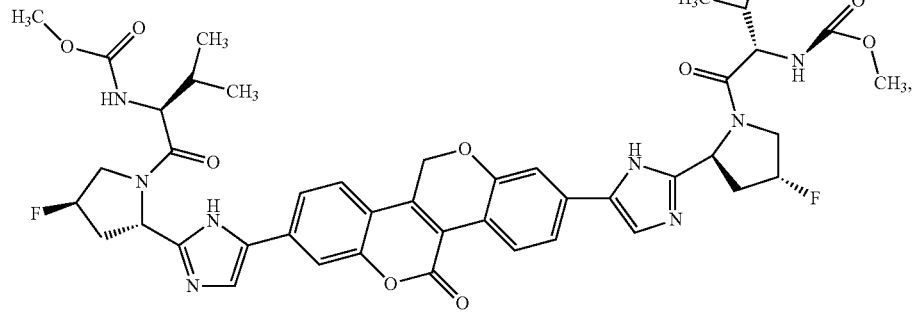
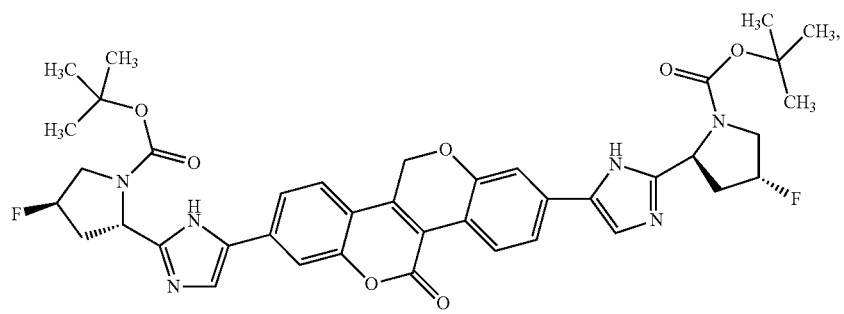
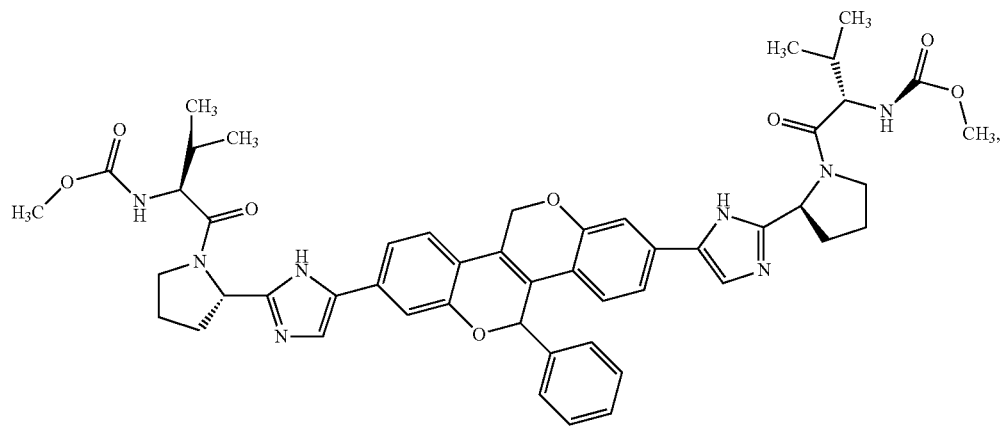
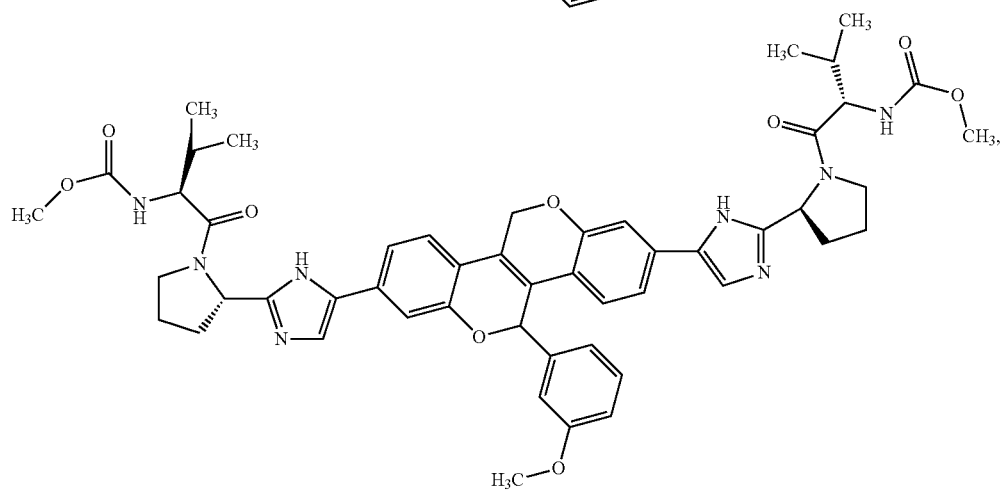

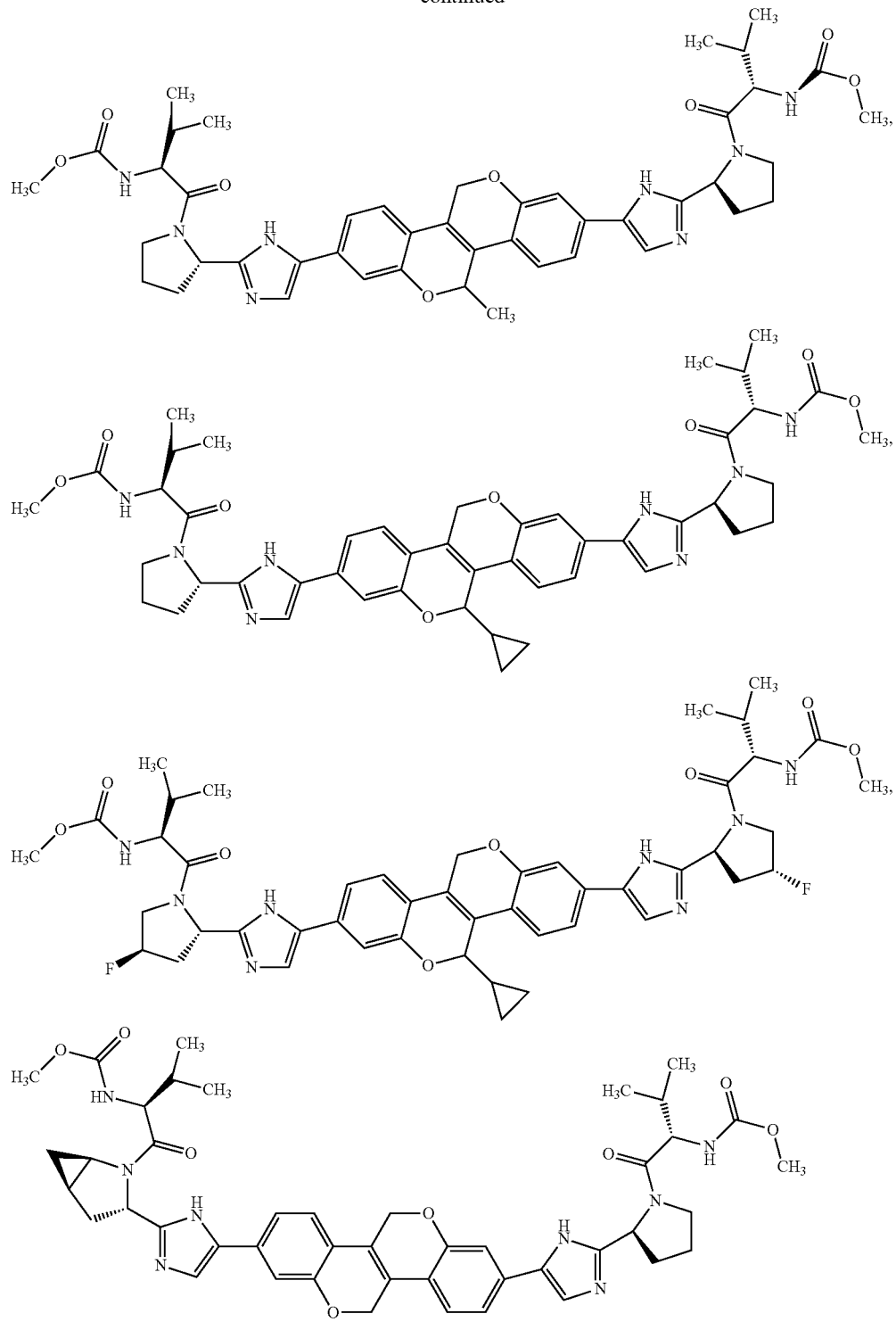

or a pharmaceutically acceptable salt thereof.

In embodiments of the invention, variables $R^1$, $R^{1A}$, $R^{1B}$, $R^{2A}$, $R^{2B}$, $R^3$, $R^7$, $R^8$, and $R^9$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, HCV NS5B polymerase inhibitors and HCV NS5A inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors, HCV NS5B polymerase inhibitors and HCV NS5A inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, HCV NS5B polymerase inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

Additional embodiments of the invention include the pharmaceutical compositions, combinations and methods set forth in (a)-(k) above and the uses set forth below, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

Further embodiments include a compound of the present invention for use (i) in, (ii) as a medicament for, or (iii) in the preparation of a medicament for: (a) medicine, (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

The Fused Tetracyclic Heterocyclic Compounds are also useful in the preparation and execution of screening assays for antiviral compounds. For example, the Fused Tetracyclic Heterocyclic Compounds are useful for identifying resistant HCV replicon cell lines harboring mutations within NS5A, which are excellent screening tools for more powerful antiviral compounds. Furthermore, the Fused Tetracyclic Heterocyclic Compounds are useful in establishing or determining the binding site of other antivirals to the HCV NS5A polymerase.

It is further to be understood that the embodiments of compositions and methods provided as (a) through (k) above are understood to include all embodiments of the compounds, including such embodiments as result from combinations of embodiments.

Treatment or Prevention of HCV Infection:

The Fused Tetracyclic Heterocyclic Compounds of the invention are useful in the inhibition of HCV, the treatment of HCV infection and/or reduction of the likelihood or severity of symptoms of HCV infection and the inhibition of HCV viral replication and/or HCV viral production in a cell-based system. For example, the Fused Tetracyclic Heterocyclic Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Fused Tetracyclic Heterocyclic Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

Combination Therapy:

In another embodiment, the present methods for treating or preventing HCV infection can further comprise the administration of one or more additional therapeutic agents which are not Fused Tetracyclic Heterocyclic Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Fused Tetracyclic Heterocyclic Compound, or a pharmaceutically acceptable salt thereof, and (ii) at least one additional therapeutic agent that is other than a Fused Tetracyclic Heterocyclic Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Fused Tetracyclic Heterocyclic Compound and an additional therapeutic agent may be present in fixed amounts (dosage amounts) in a single dosage unit (e.g., a capsule, a tablet and the like).

In one embodiment, the at least one Fused Tetracyclic Heterocyclic Compound is administered during a time when the additional therapeutic agent(s) exert their prophylactic or therapeutic effect, or vice versa.

In another embodiment, the at least one Fused Tetracyclic Heterocyclic Compound and the additional therapeutic agent(s) are administered in doses commonly employed when such agents are used as monotherapy for treating a viral infection.

In another embodiment, the at least one Fused Tetracyclic Heterocyclic Compound and the additional therapeutic agent(s) are administered in doses lower than the doses commonly employed when such agents are used as monotherapy for treating a viral infection.

In still another embodiment, the at least one Fused Tetracyclic Heterocyclic Compound and the additional therapeutic agent(s) act synergistically and are administered in doses lower than the doses commonly employed when such agents are used as monotherapy for treating a viral infection.

In one embodiment, the at least one Fused Tetracyclic Heterocyclic Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Fused Tetracyclic Heterocyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Fused Tetracyclic Heterocyclic Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, one or more compounds of the invention are administered with one or more additional therapeutic agents, including but not limited to the therapeutic agents described, supra.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In another embodiment, one or more compounds of the present invention are administered with one additional therapeutic agent selected from an HCV protease inhibitor, an interferon, a pegylated interferon and ribavirin. In another embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716 (ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., Current Opinion in Drug Discovery and Development, 7(4):446 (2004); Tan et al., Nature Reviews, 1:867 (2002); and Beaulieu et al., Current Opinion in Investigational Drugs, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

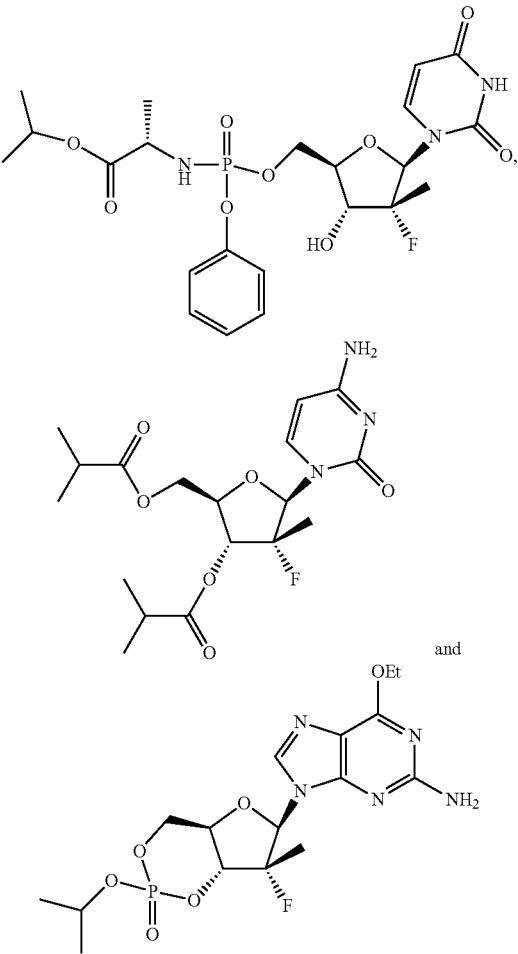

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J. in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhbitors useful in the present compositions and methods include, but are not limited to, an HCV protease inhibitor.

Examples of HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

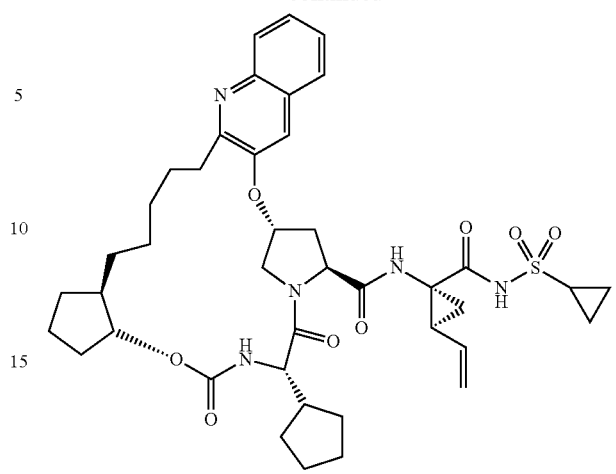

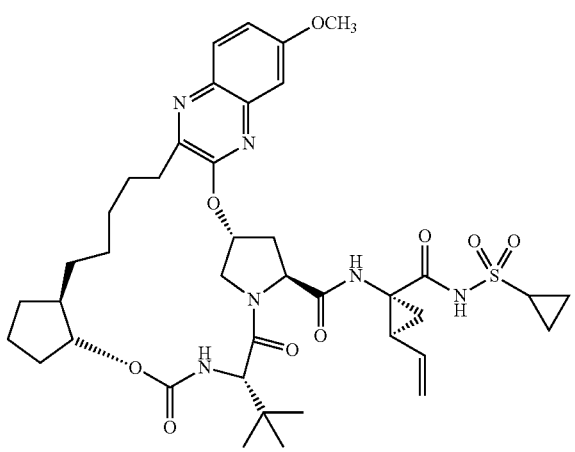

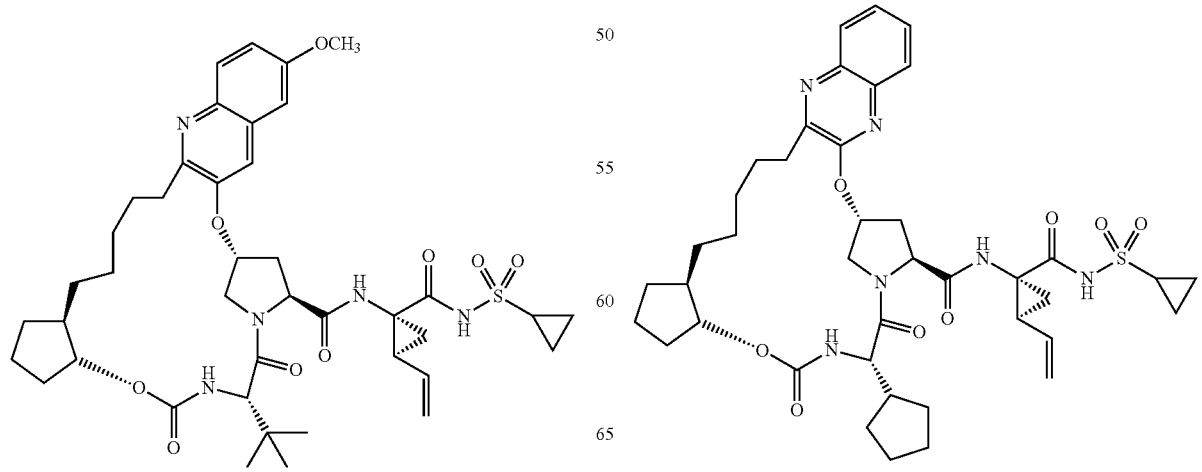

39
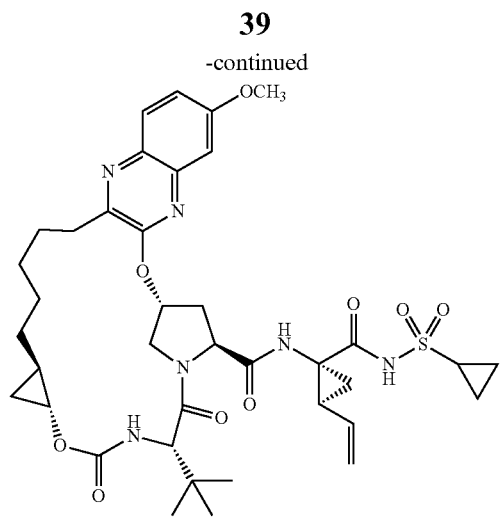
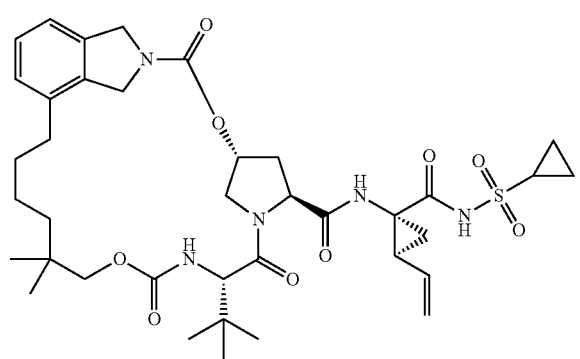
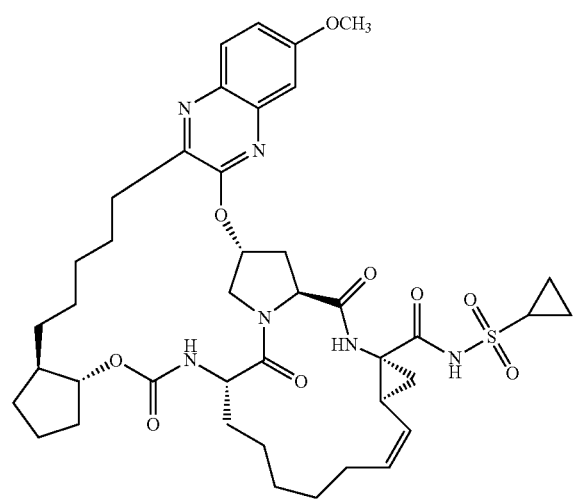
40
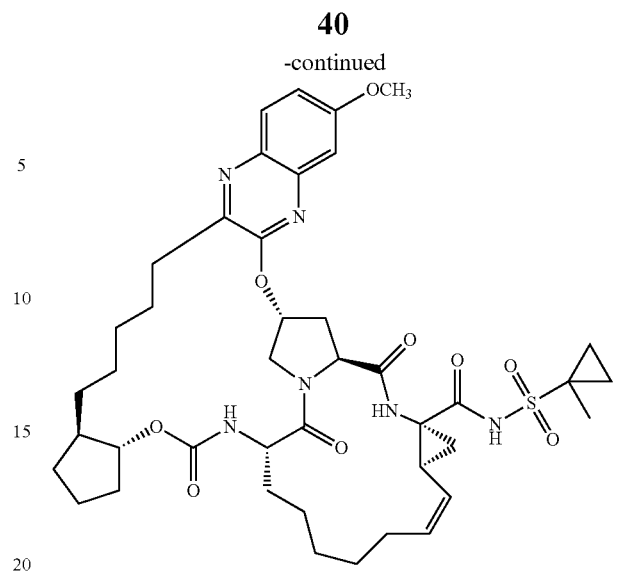
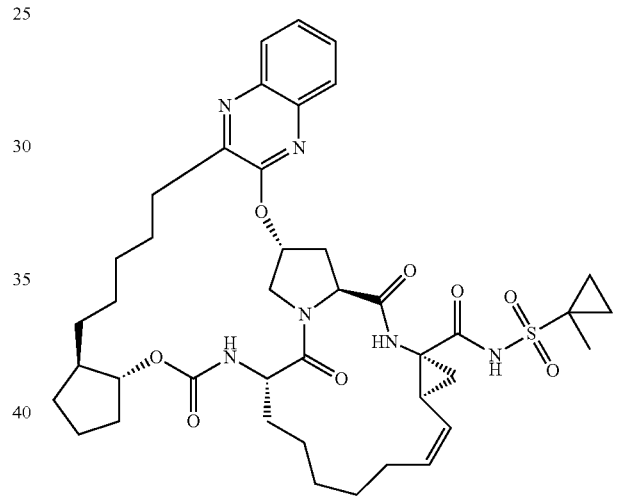
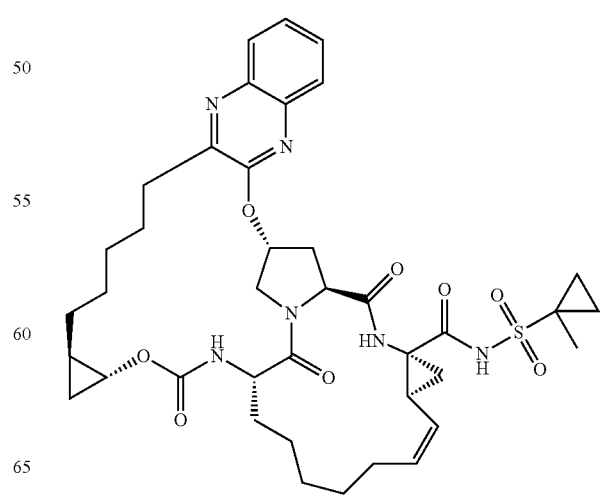

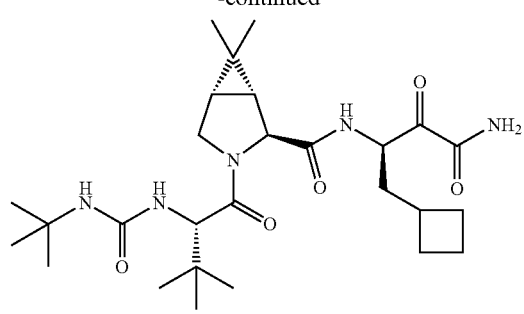
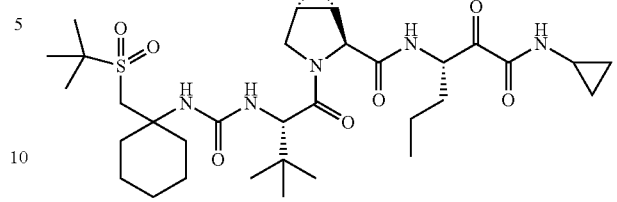
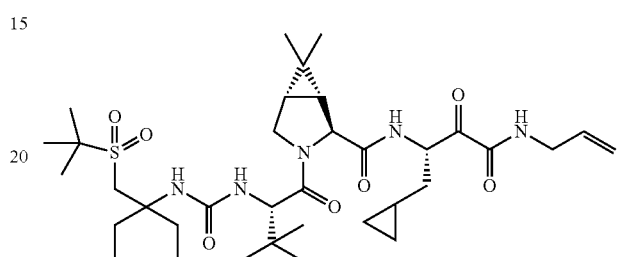
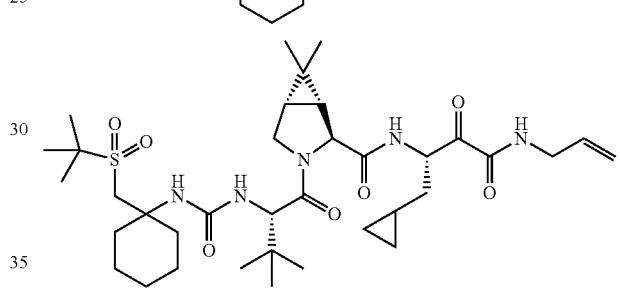
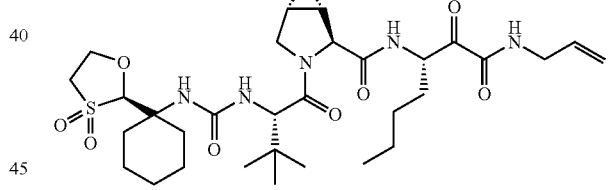
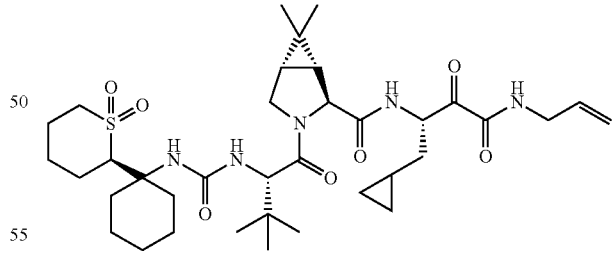
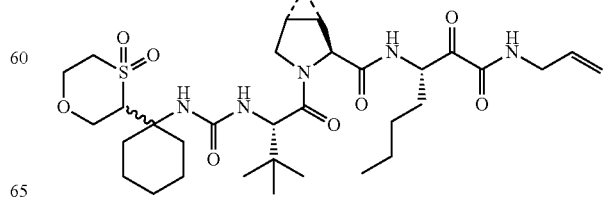

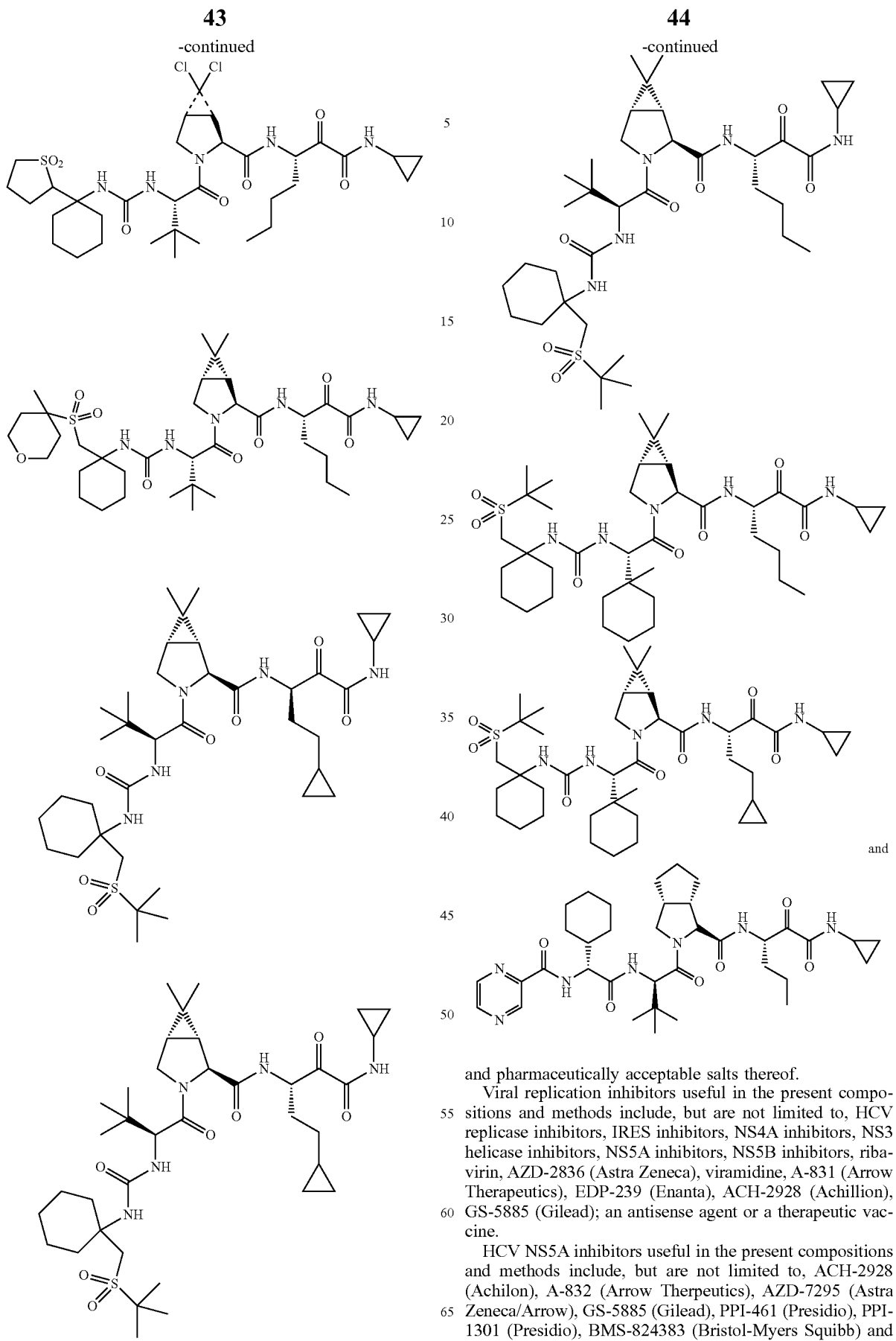

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS5A inhibitors useful as second additional therapeutic agents in the present compositions and methods include, but are not limited to those disclosed in International Publication No. WO 2010/111483 and the following compounds:
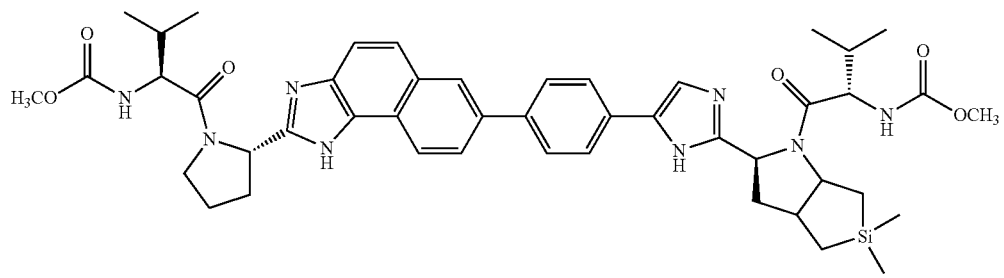
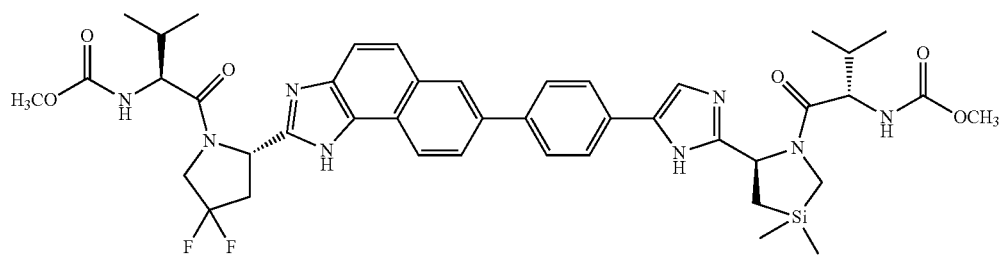
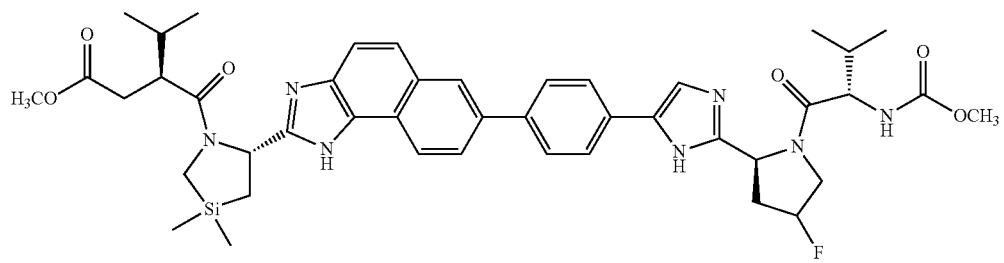
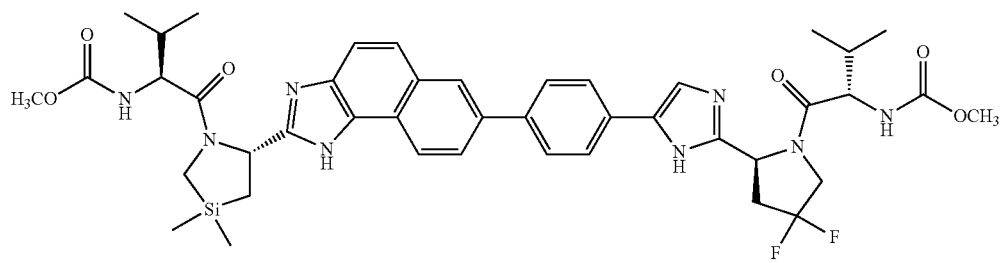
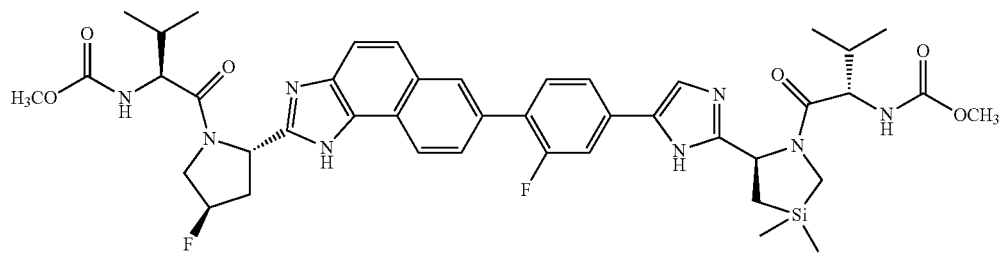
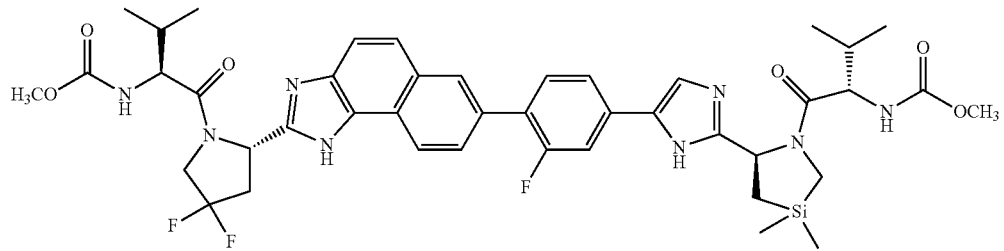

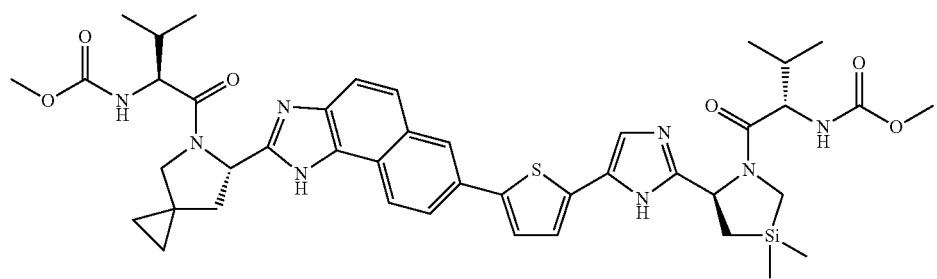
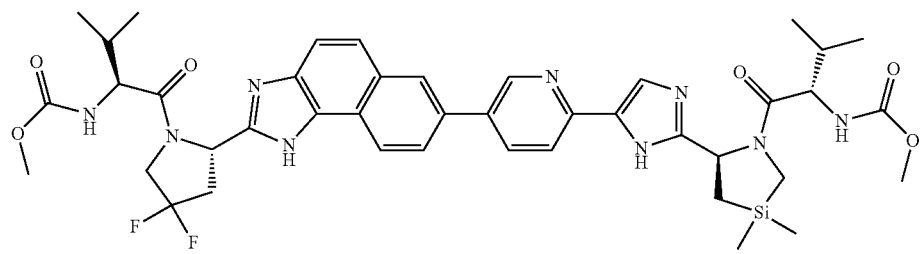
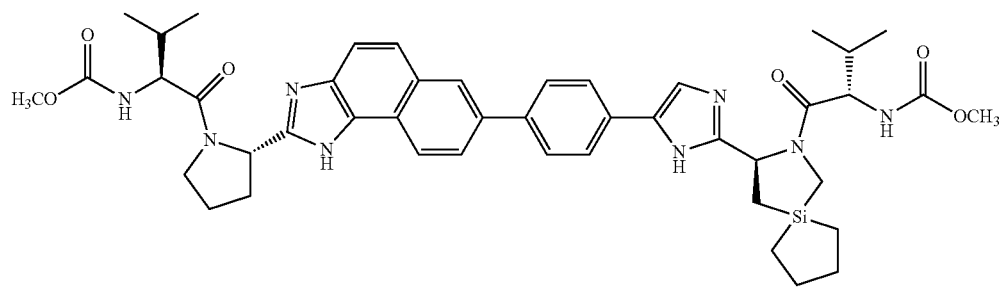
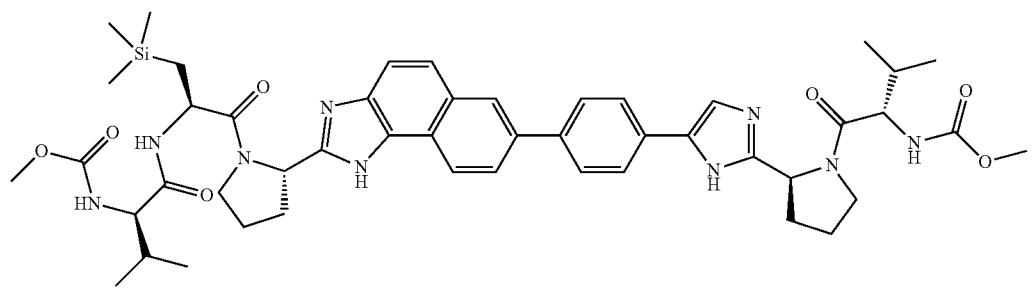
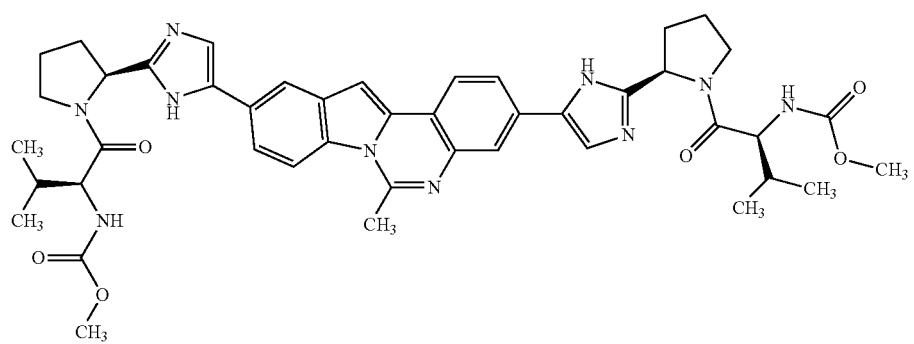

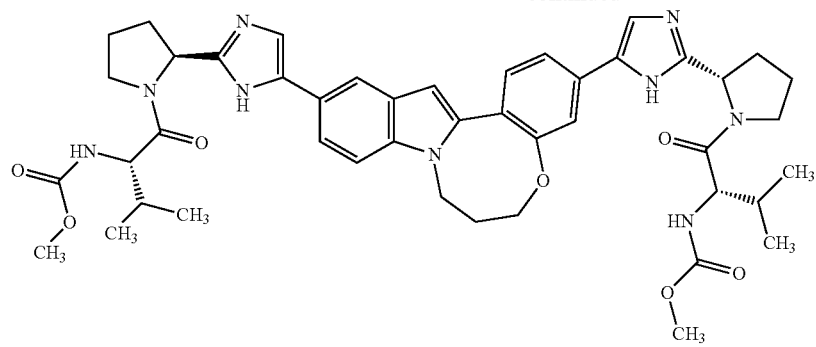
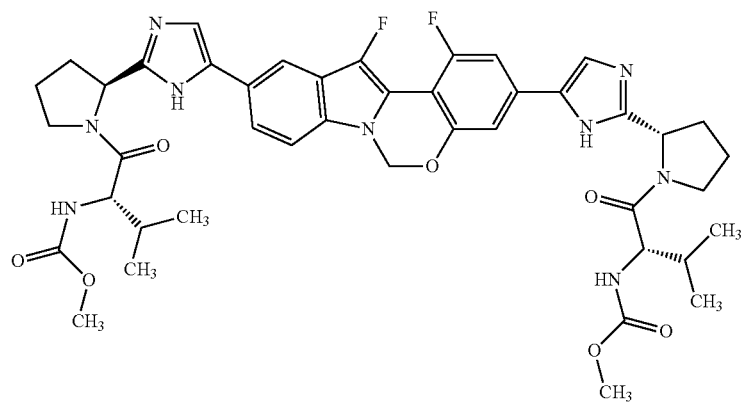
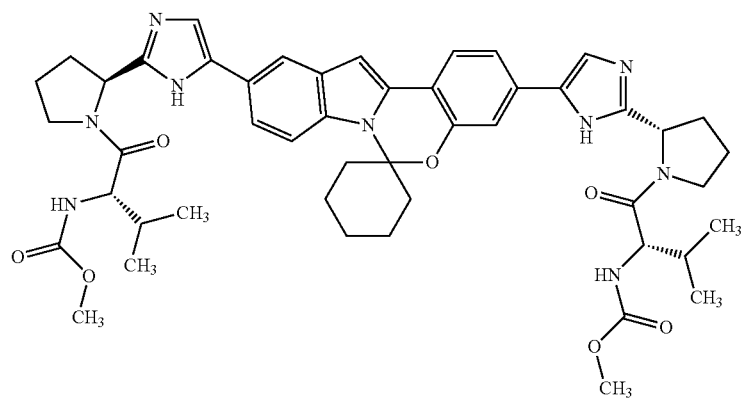
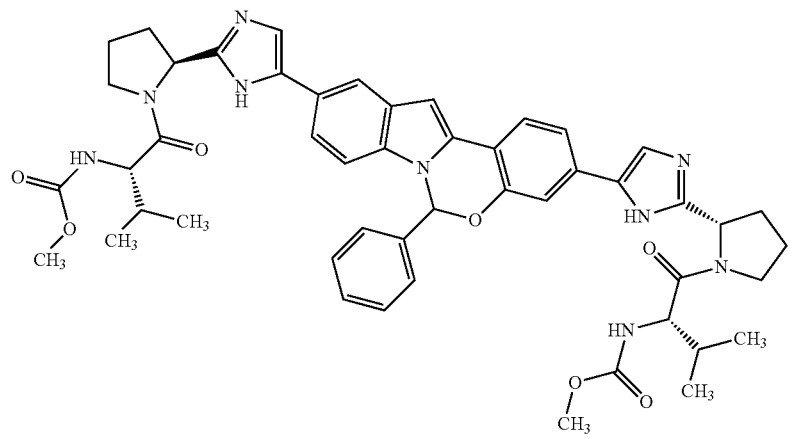

-continued
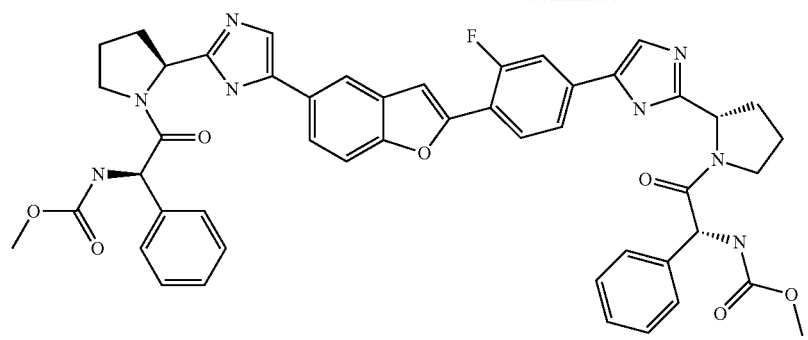
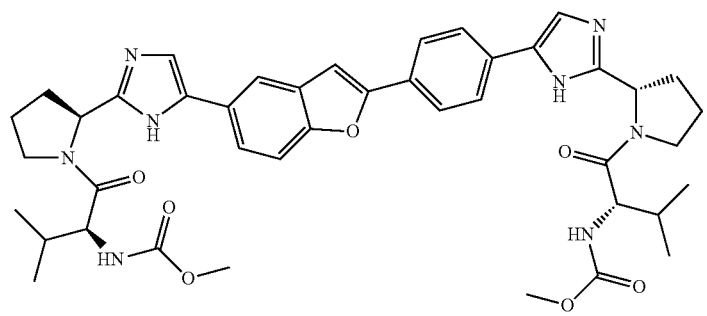
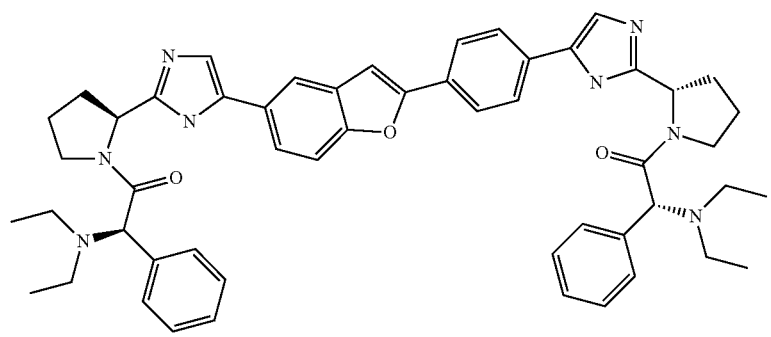
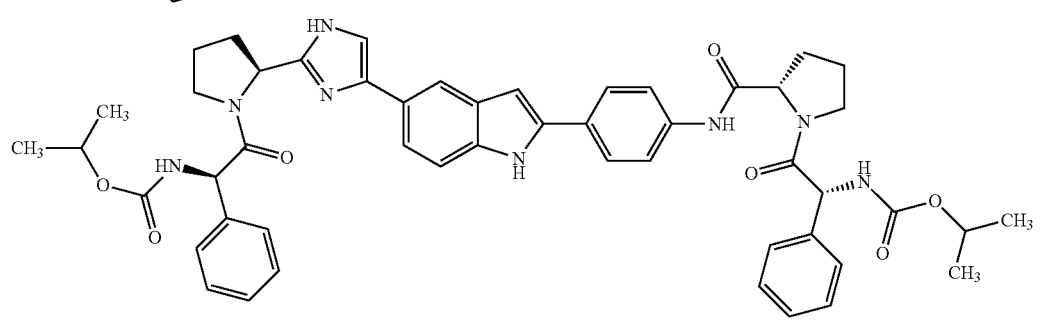
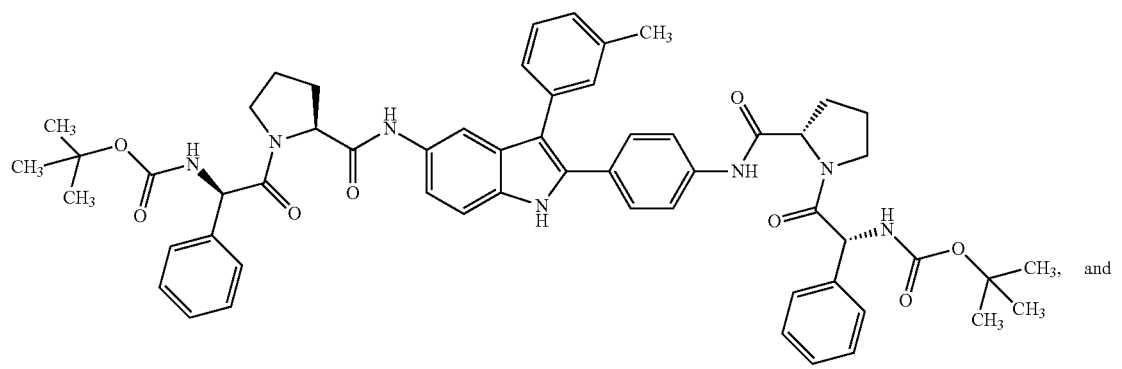
and

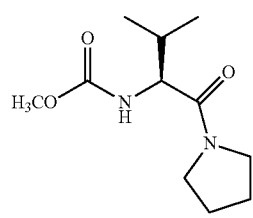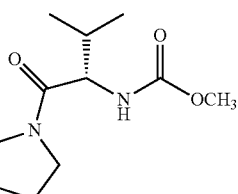

and pharmaceutically acceptable salts thereof.

HCV replicase inhibitors useful in the present compositions and methods include, but are not limited to, those disclosed in U.S. Patent Publication No. US20090081636.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Fused Tetracyclic Heterocyclic Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

When administered to a patient, the Fused Tetracyclic Heterocyclic Compounds can be administered as a component of a composition that comprises a pharmaceutically acceptable carrier or vehicle. The present invention provides pharmaceutical compositions comprising an effective amount of at least one Fused Tetracyclic Heterocyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Tetracyclic Heterocyclic Compounds are administered orally.

In another embodiment, the one or more Fused Tetracyclic Heterocyclic Compounds are administered intravenously.

In one embodiment, a pharmaceutical preparation comprising at least one Fused Tetracyclic Heterocyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tetracyclic Heterocyclic Compound(s) by weight or volume. In various embodiments, the present compositions can contain, in one embodiment, from about 1% to about 70% or from about 5% to about 60% of the Fused Tetracyclic Heterocyclic Compound(s) by weight or volume.

Generally, a total daily dosage of the at least one Fused Tetracyclic Heterocyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

The amount and frequency of administration of the Fused Tetracyclic Heterocyclic Compounds will be regulated according to the judgment of the attending clinician considering such factors as age, condition and size of the patient as well as severity of the symptoms being treated.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The compositions of the invention can further comprise one or more additional therapeutic agents, selected from those listed above herein. Accordingly, in one embodiment, the present invention provides compositions comprising: (i) at least one Fused Tetracyclic Heterocyclic Compound or a pharmaceutically acceptable salt thereof; (ii) one or more additional therapeutic agents that are not a Fused Tetracyclic Heterocyclic Compound; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and two additional therapeutic agents, each of which are independently selected from the group consisting of HCV antiviral agents, immunomodulators, and anti-infective agents.

Methods for Making the Compounds of Formula (I):

The Compounds of Formula (I) may be prepared from known or readily prepared starting materials, following methods known to one skilled in the art of organic synthesis. Methods useful for making the Compounds of Formula (I) are set forth in the Examples below and generalized in Scheme 1 below. Alternative synthetic pathways and analogous structures will be apparent to those skilled in the art of organic synthesis.

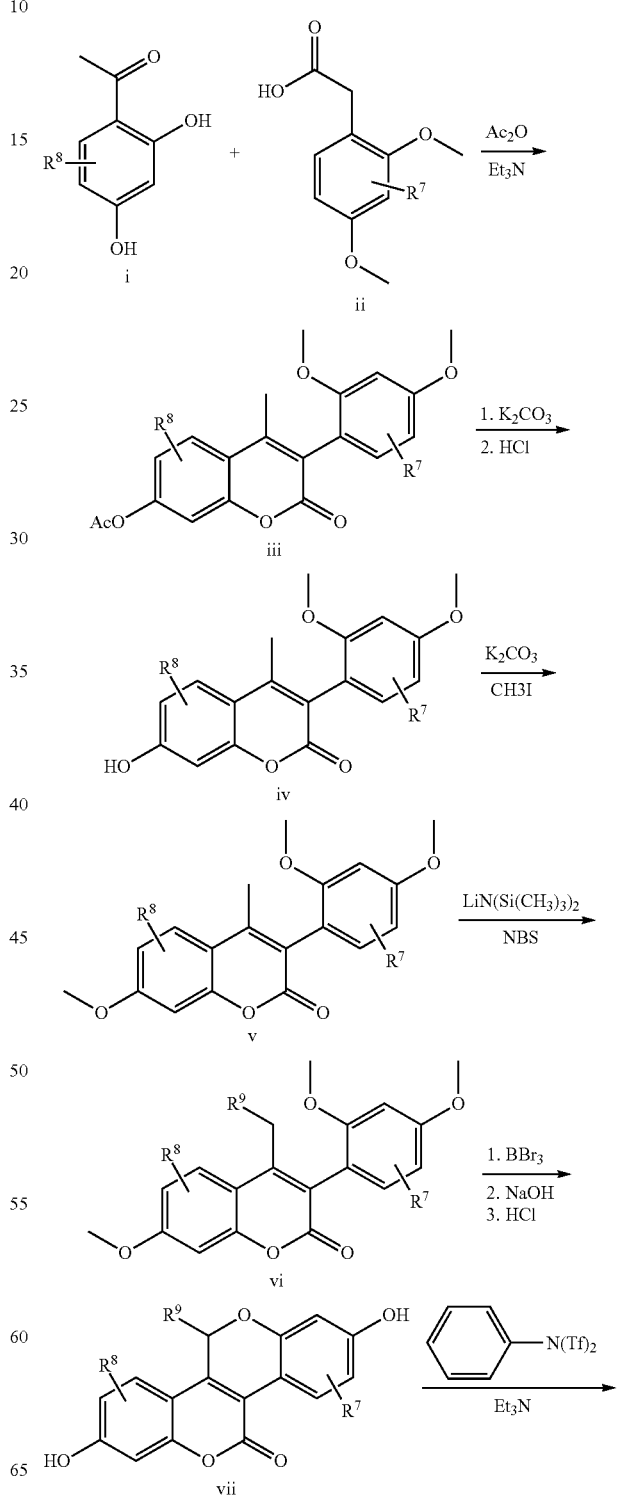

Scheme 1

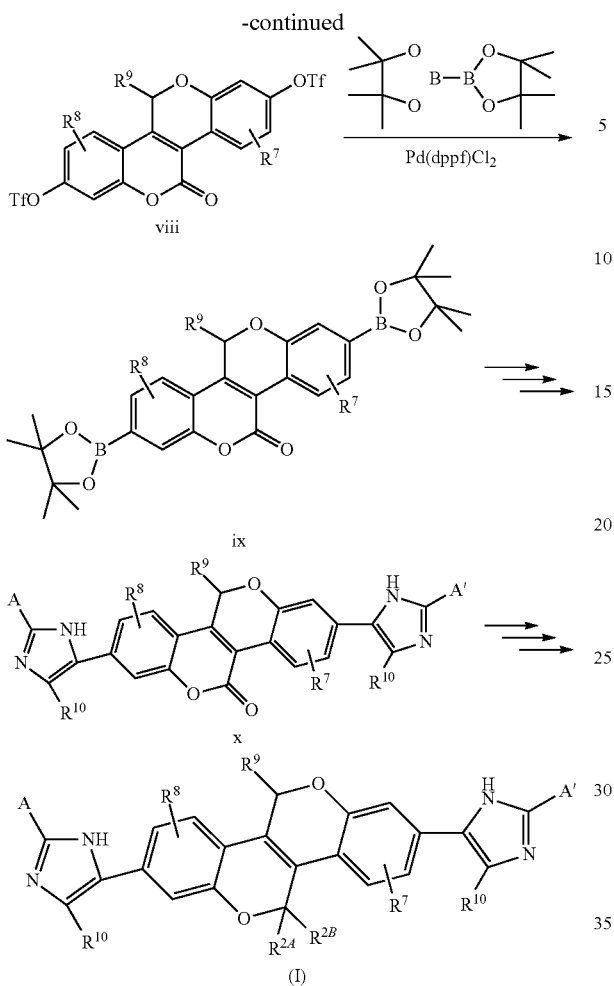

Wherein A, A', $R^{2A}$, $R^{2B}$, $R^7$, $R^8$, $R^9$, and $R^{10}$ are defined herein for the Compounds of Formula (I).

1-(2,4-dihydroxyphenyl)ethanone (i) can be reacted with 2,4-dimethoxybenzoic acid (ii) in the presence of acetic anhydride and triethylamine to form the 2-oxo chromene compound of formula iii. The acetate group of iii can then be removed using a carbonate base, followed by acidification using HCl to provide aryl alcohol iv which is subsequently converted to its corresponding methoxy derivative v using methyl iodide in the presence of a base. Bromination of the methyl group of v using N-bromosuccinimide provides the methyl bromide compound vi which is then cyclized to provide tetracyclic ketone vii. Conversion of vii to the corresponding ditriflate viii using N,N-bis(trifluoromethanesulfonyl)aniline in the presence of a base and subsequent treatment of viii with bis(pinacol)diboroane and a palladium (II) catalyst provides the diboronic acid compound ix. Compound ix can then be derivatized to incorporate groups A and A' and provide ketone compound x using methods well-known in the art, and described in the Examples below, for making HCV NS5A inhibitors. A compound of formula x can then be converted to the compounds of formula (I) via derivatization of the ketone moiety of x using methods well-known in the art of organic synthesis.

Compounds of Formula (I) may be further elaborated using methods that would be well-known to those skilled in the art of organic synthesis or, for example, the methods described in the Examples below, to make the full scope of the Compounds of Formula (I).

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene et al., supra.

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Scheme 1 may be isolated and purified if desired using conventional techniques, including but not limited to filtration, distillation, crystallization, chromatography and the like. Such materials can be characterized using conventional means, including physical constants and spectral data.

Example 1

Preparation of Compound Cap 1

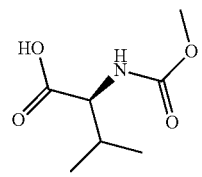

Step 1—Synthesis of Compound Cap 1.

Compound cap 1 was prepared as described in Example 4 of WO 2012/040923.

Example 2

Preparation of Compound Cap 2

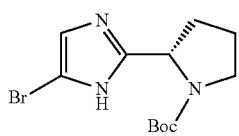

Step 1—Synthesis of Compound Cap 2.

Compound cap 2 was prepared as described in Example 7 of WO 2012/040923.

Example 3
Preparation of Compound Cap 3
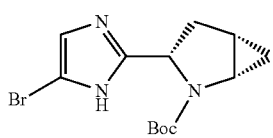
cap 3
Step 1—Synthesis of Compound Cap 3.
Compound cap 3 was prepared as described in Example 12A of WO2012/041014.
Example 4
Preparation of Compound Cap 4
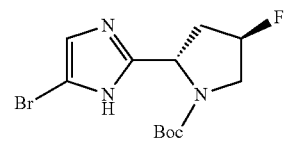
cap 4
Step 1—Synthesis of Compound Cap 4.
Compound cap 4 was prepared as described in Example 10 of WO 2012/041014.
Example 5
Preparation of Compound 1
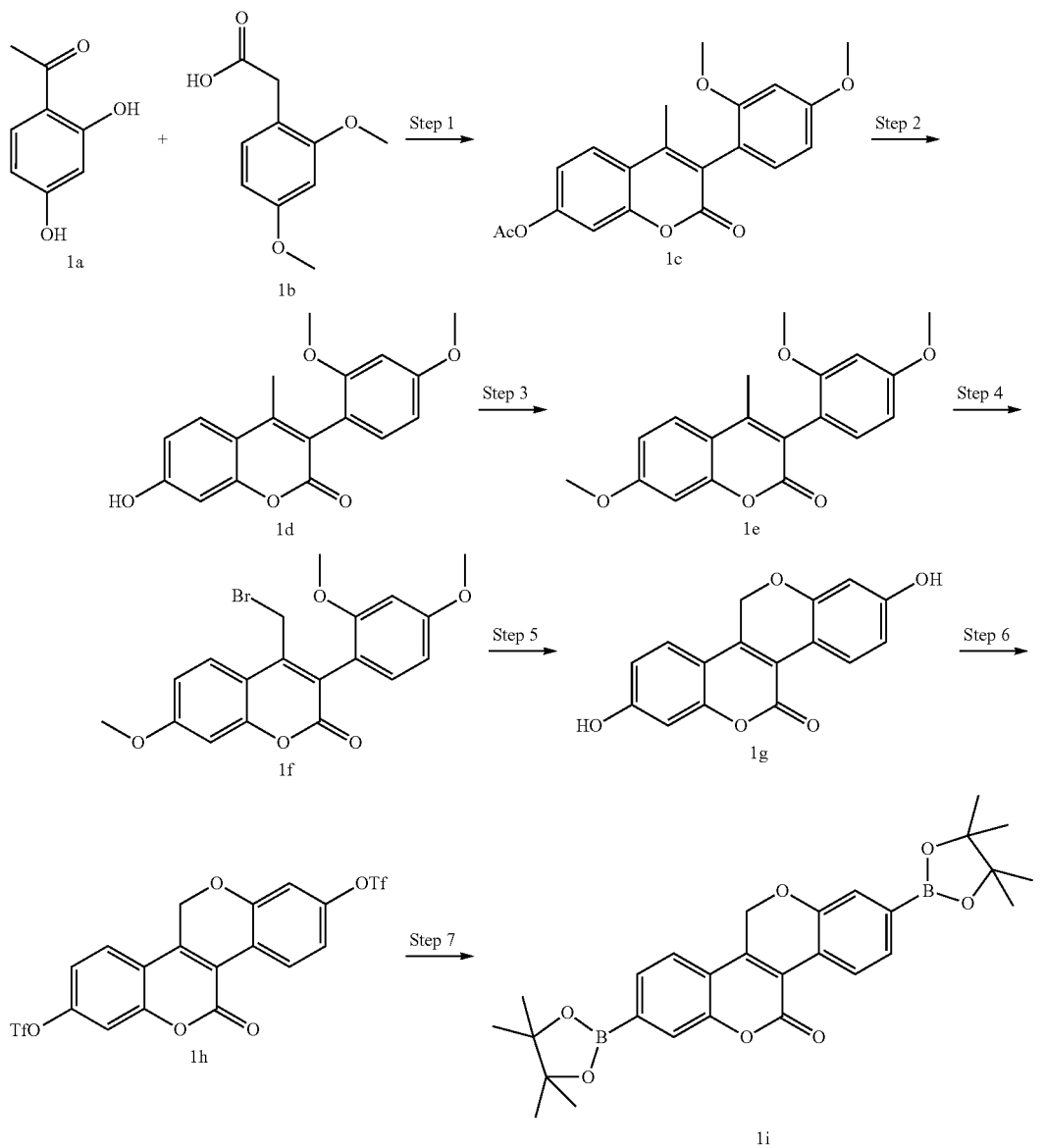

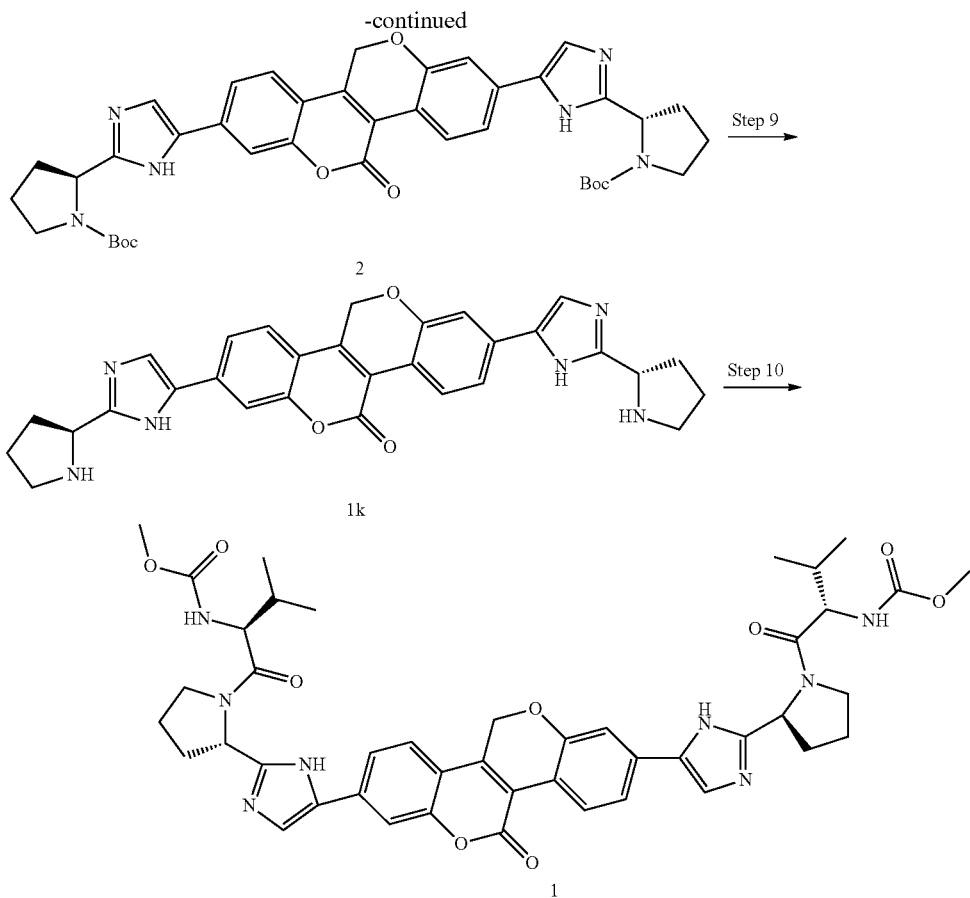

Step 1—Synthesis of Compound 1c

To a mixture of compound 1a (17.4 g, 110 mmol), compound 1b (22.4 g, 110 mmol) and acetic anhydride (58 g, 570 mmol) with agitation under a nitrogen atmosphere was added triethylamine (58 mL, 110 mmol) dropwise. The reaction mixture was heated to 148° C. for 24 hours. The excess reagents were removed by distillation under reduced pressure and the residue was diluted with ether (30 mL). The solid was collected by filtration and washed with ether to afford compound 1c (30 g, 79%).

Step 2—Synthesis of Compound 1d

A mixture of compound 1c (2.5 g, 7.3 mmol), MeOH (12 ml) and $K_2CO_3$ (1.3 g, 9 mmol) was heated to reflux at 65° C. for 1.5 hours. The mixture was diluted with EtOAc (30 mL) and treated with 2 N HCl. The organic phase was separated and concentrated to afford compound 1d (2.1 g, 91%).

Step 3—Synthesis of Compound 1e

To a mixture of compound 1d (2.1 g, 6.7 mmol) and $K_2CO_3$ (2.8 g, 20.2 mmol) in DMF (10 mL) was added MeI (1.2 g, 8.7 mmol) dropwise. The reaction mixture was heated to reflux at 20° C. for 2 hours. The reaction mixture was cooled to 0° C. and diluted with water, extracted with EtOAc. The organic phase was concentrated in vacuo, and the residue was purified by $SiO_2$ chromatography, eluting with petroleum ether: ethyl acetate (100/1~10/1) to afford the desired compound 1e (1.5 g, 71%).

Step 4—Synthesis of Compound 1f

To a mixture of compound 1e (730 mg, 2.2 mmol) in THF (30 ml) with agitation under a nitrogen atmosphere, was added lithium bis(trimethylsilyl)amide (2.4 mL, 2.4 mmol, 1 M in THF) dropwise at −30° C. The reaction mixture was stirred for 1 hour at −30° C. and then cooled to −76° C. Meantime, the NBS (434 mg, 2.4 mmol) in THF (15 ml) was cooled to −76° C. With fast agitation, the above solution of compound 1e was quickly transferred into NBS/THF solution. The reaction was stirred at −76° C. for 1 hour. The reaction mixture was added saturated solution of $Na_2S_2O_3$, washed with 1 N HCl and extracted with EtOAc. The organic phase was concentrated in vacuo, and the residue was purified by $SiO_2$ chromatography, eluting with petroleum ether: ethyl acetate (100/1~10/1) to afford the desired compound 1f (400 mg, 44%).

Step 5—Synthesis of Compound 1g

To a mixture of compound 1f (560 mg, 1.4 mmol) in $CH_2Cl_2$ (25 ml) with agitation under a nitrogen atmosphere, was added $BBr_3$ (1.7 g, 7.2 mmol) dropwise at 0° C. The reaction mixture was refluxed for 24 hours at 20° C. The reaction mixture was added saturated $NaHCO_3$ and $H_2O$, the pH of reaction solution was adjusted to 12 by adding 10 N NaOH and stirred at room temperature for 2 hours. The pH of aqueous layer was adjusted to 1 by the addition of concentrated HCl. After filtration, the solid was washed with water to afford compound 1g (260 mg, 78%).

Step 6—Synthesis of Compound 1h

To the solution of compound 1g (600 mg, 2.1 mmol) and TEA (0.7 mL, 4.9 mmol) in DCM (20 ml) was added N,N-bis (trifluoromethanesulfonyl) aniline (1.5 g, 4.2 mmol), and stirred at room temperature for 24 hours. The mixture was concentrated in vacuo and purified by chromatography on silica to give the compound 1h (400 mg, 36% yield).

Step 7—Synthesis of Compound 1i

To a solution of 1h (0.4 g, 0.72 mmol) in 1,4-dioxane was added bis pinacol borate (0.41 g, 1.6 mmol) and Pd(dppf)Cl$_2$ (0.052 g, 0.072 mmol) and KOAc (0.28 g, 2.8 mmol). The reaction mixture was stirred under N$_2$ and heated to 110° C. overnight. The solvent was then removed under vacuum, and the residue was purified by SiO$_2$ chromatography, eluting with petroleum ether: ethyl acetate (20/1~5/1) to afford the product ii (0.3 g, 83%).

Step 8—Synthesis of Compound 2

A suspension of 1i (300 mg, 0.6 mmol), Cap2 (415 mg, 1.3 mmol), Pd(dppf)$_2$Cl$_2$ (44 mg, 0.03 mmol), Na$_2$CO$_3$ (0.318 g, 3 mmol) and in THF/H$_2$O (10:1, 25 mL) was refluxed at 95° C. overnight under N$_2$ protection. After that, the mixture was filtered, and the filtrate was washed with water (50 mL) and extracted with EtOAc (100 mL). The organic layer was washed with brine and dried over anhydrous sodium sulfate. After filtration and concentration, the residue was purified by SiO$_2$ chromatography, eluting with DCM: methanol (100/1~50/1) to afford compound 2 (0.15 g).

Step 9—Synthesis of Compound 1k

To a solution of 2 (0.12 g, 0.17 mmol) in 1,4-dioxane (5 mL) was added HCl/1,4-dioxane (2 mL, 3M). Then the mixture was stirred at room temperature for 1 hour. When the reaction was complete, the mixture was concentrated in vacuum to afford compound 1k (0.1 g, 99%).

Step 10—Synthesis of Compound 1

To a mixture of 1k (100 mg, 0.19 mmol), Cap 1 (673 mg, 0.38 mmol) and HATU (150 mg, 0.38 mmol) in DMF (3 mL) was added DIEA (120 mg, 1 mmol). The resulting mixture was stirred at room temperature for 30 minutes, and LC-MS judged the material was consumed. After filtration, the filtrate was purified by Pre-HPLC to yield compound 1 (50 mg). $^1$H-NMR (MeOD) δ: 8.53-8.61 (m, 1H), 7.64-7.97 (m, 4H), 7.23-7.44 (m, 2H), 5.42-5.48 (m, 2H), 5.19-5.23 (m, 2H), 4.22-4.23 (d, J=4 Hz, 2H), 3.99-4.10 (m, 2H), 3.85-3.91 (m, 2H), 3.62-3.64 (m, 6H), 2.50-2.54 (m, 2H), 2.26 (s, 2H), 2.06-2.15 (m, 6H), 0.90-0.98 (m, 12H). LC/MS: Anal. Calcd. For [M+H]$^+$ C$_{44}$H$_{50}$N$_8$O$_9$: 834.94; found 835.6.

Example 6

Preparation of Compound 3

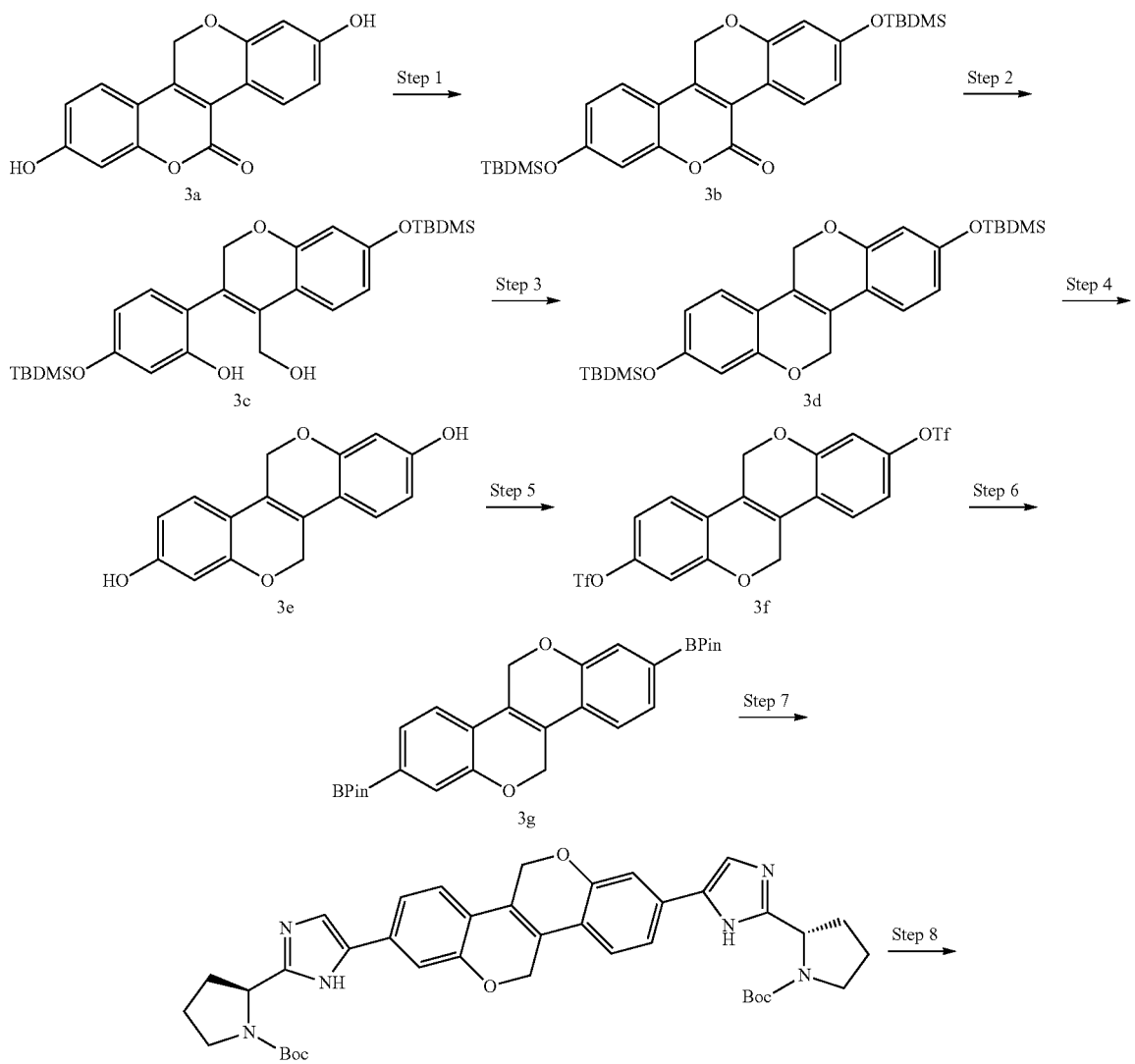

-continued

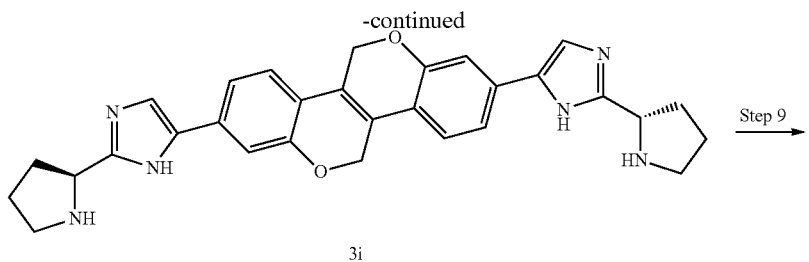

3i

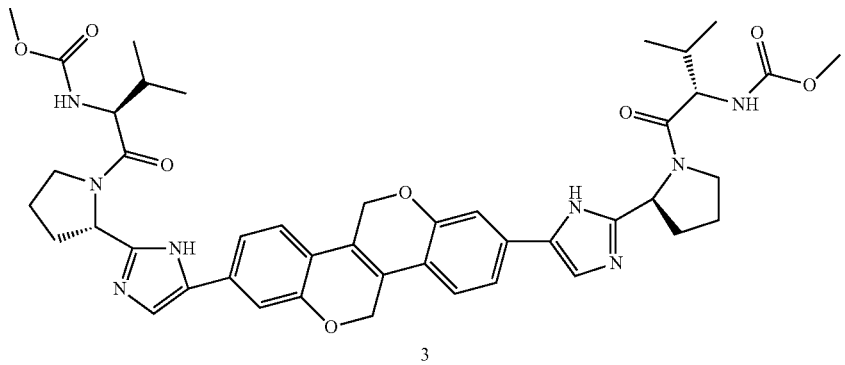

3

Step 1—Synthesis of Compound 3b

Compound 3a was prepared as described in Example 5 (see compound 1g).

To a mixture of compound 3a (260 mg, 0.88 mmol) and Et$_3$N (0.3 mL, 1.8 mol) in CH$_2$Cl$_2$ (10 ml) with agitation under a nitrogen atmosphere, was added TBDMSCl (280 mg, 1.7 mmol) dropwise. The reaction mixture was stirred at room temperature for 24 hours. To the reaction mixture was added saturated NaHCO$_3$ and washed with 1 N HCl. The organic phase was concentrated to afford compound 3b (260 mg, 78%).

Step 2—Synthesis of Compound 3c

To a mixture of LiAlH$_4$ (14 mg, 0.38 mmol) in THF (7 ml) with agitation under a nitrogen atmosphere, was added compound 3b (100 mg, 019 mmol) in THF (3 ml) dropwise at 0° C. The reaction mixture was stirred at room temperature for 30 minutes. The reaction mixture was added in saturated Na$_2$SO$_4$ and extracted by EtOAc. The mixture was concentrated in vacuo and purified by SiO$_2$ chromatography, eluting with petroleum ether: ethyl acetate (10/1~2/1) to afford the compound 3c (80 mg, 82%).

Step 3—Synthesis of Compound 3d

To a mixture of PPh$_3$ (2.7 g, 10.4 mmol) in THF (150 ml) with agitation under a nitrogen atmosphere, was added DEAD (1.8 g, 10.4 mmol) dropwise at 0° C. The reaction mixture was stirred at room temperature for 30 minutes. Then the mixture was cooled to 0° C. and compound 3c (4.1 g, 8.0 mmol) in THF (100 mL) was added dropwise. The reaction mixture was stirred at room temperature for 2 hours. The mixture was concentrated in vacuo and purified by SiO$_2$ chromatography, eluting with petroleum ether: ethyl acetate (30/1~5/1) to afford the compound 3d (2 g, 50%).

Step 4—Synthesis of Compound 3e

A mixture of compound 3d (420 mg, 0.85 mmol) and TBAF (589 mg, 1.69 mmol) in THF (20 mL) was stirred for 30 minutes at room temperature. The reaction mixture was washed with 1 N HCl and extracted by EtOAc. The organic phase was concentrated to afford compound 3e (200 mg, 88%).

Step 5—Synthesis of Compound 3f

To a solution of compound 3e (260 mg, 0.9 mmol) and TEA (0.3 mL, 2.1 mmol) in DCM (10 ml) was added N,N-bis (trifluoromethanesulfonyl) aniline (649 mg, 1.8 mmol). The solution was stirred at room temperature for 24 hours. The mixture was concentrated in vacuo and purified by chromatography on silica to give the compound 3f (110 mg, 23%).

Step 6—Synthesis of Compound 3g

To a solution of compound 3f (0.7 g, 1.3 mmol) in 1,4-dioxane was added bis pinacol borate (0.76 g, 3 mmol) and Pd(dppf)Cl$_2$ (0.095 g, 0.13 mmol) and KOAc (0.5 g, 5.2 mmol). The reaction mixture was stirred under N$_2$ and heated to 110° C. overnight. After that, the solvent was removed under vacuum, and the residue was purified by SiO$_2$ chromatography, eluting with petroleum ether: ethyl acetate (20/1~5/1) to afford the product 3g (0.4 g, 63%).

Step 7—Synthesis of Compound 4

A suspension of 3g (382 mg, 0.78 mmol), Cap2 (542 mg, 1.7 mmol), Pd(dppf)$_2$Cl$_2$ (57 mg, 0.03 mmol), Na$_2$CO$_3$ (0.413 g, 3.9 mmol) and in THF/H$_2$O (10:1, 25 mL) was refluxed at 95° C. overnight under N$_2$ protection. After that, the mixture was filtered, and the filtrate was washed with water (50 mL) and extracted with EtOAc (100 mL). The organic layer was washed with brine and dried over anhydrous sodium sulfate. After filtration and concentration, the residue was purified by SiO$_2$ chromatography, eluting with DCM: methanol (100/1~50/1) to afford the compound 4 (0.26 g).

Step 8—Synthesis of Compound 3i

To a solution of 4 (0.26 g, 0.37 mmol) in 1,4-dioxane (5 mL) was added HCl/1,4-dioxane (2 mL, 3M). Then the mixture was stirred at room temperature for 1 hour. When the reaction completed, the mixture was concentrated in vacuum to yield compound 3i (0.2 g, 99%).

Step 9—Synthesis of Compound 3

To a mixture of 3i (200 mg, 0.37 mmol), Cap 1 (138 mg, 0.78 mmol) and HATU (310 mg, 0.78 mmol) in DMF (5 mL) was added DIEA (240 mg, 2 mmol). The resulting mixture was stirred at room temperature for 30 min, and LC-MS judged the material was consumed up. After filtration, the filtrate was purified by Pre-HPLC to afford compound 3 (100 mg). $^1$H-NMR (MeOD) δ: 7.80-7.86 (m, 2H), 7.17-7.31 (m, 6H), 5.18-5.21 (m, 6H), 4.20-4.22 (d, J=8 Hz, 2H), 4.02-408 (m, 2H), 3.85-3.87 (m, 2H), 3.62-3.63 (s, 6H), 2.25 (s, 2H), 2.02-2.25 (m, 8H), 0.87-0.93 (m, 12H). LC/MS: Anal. Calcd. For [M+H]$^+$ C$_{44}$H$_{52}$N$_8$O$_8$: 820.95; found 821.8.

Example 7

Preparation of Compound 7

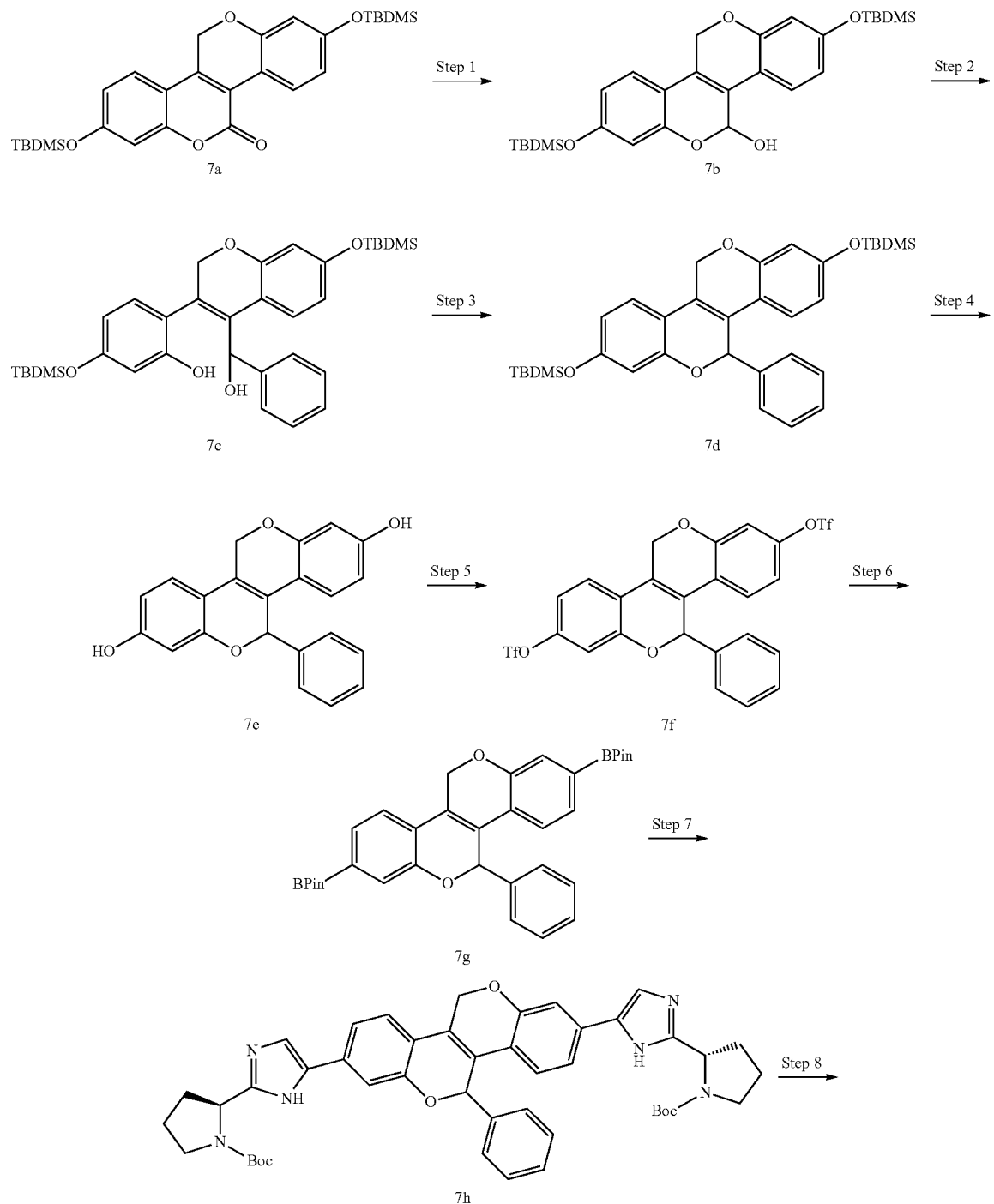

-continued

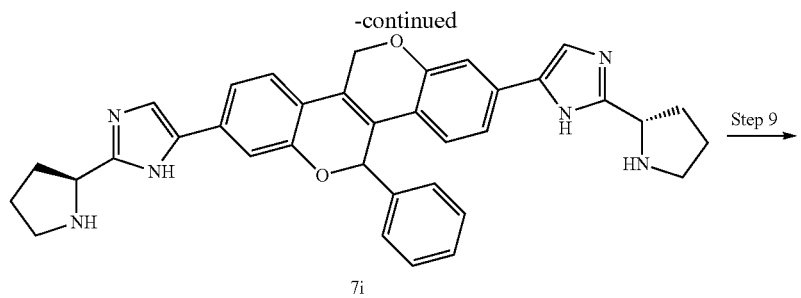

7i

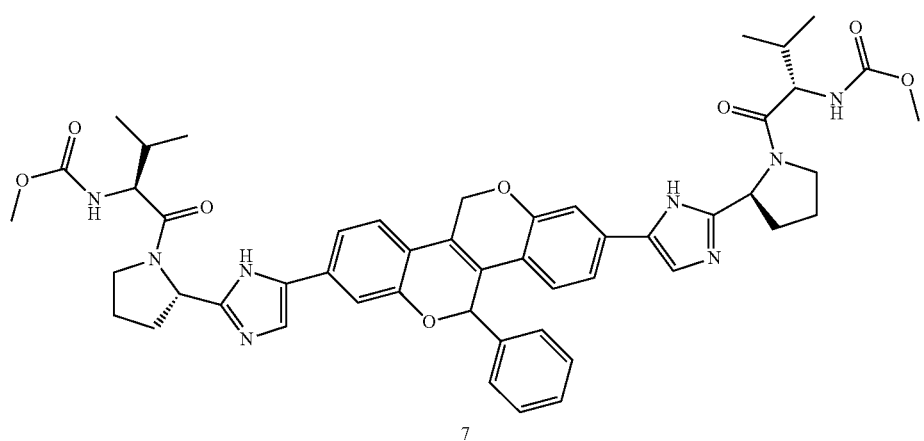

7

Step 1—Synthesis of Compound 7b

Compound 7a was prepared as described in Example 6.

To a mixture of compound 7a (200 mg, 0.39 mmol) in $CH_2Cl_2$ (10 ml) under a nitrogen atmosphere at 40° C., was added DIBALH (0.47 mL, 0.47 mmol) dropwise. The reaction mixture was stirred for 1.5 hours at 40° C. The reaction mixture was quenched saturated $Na_2SO_4$ and extracted by $CH_2Cl_2$. The organic phase was concentrated and purified by $SiO_2$ chromatography, eluting with petroleum ether: ethyl acetate (20/1~3/1) to yield 7b (110 mg, 57%).

Step 2—Synthesis of Compound 7c

To a mixture of compound 7b (100 mg, 0.2 mmol) in THF (10 ml) under a nitrogen atmosphere at 0° C., was added PhMgBr (1.5 ml, 1 mmol) dropwise. The reaction mixture was stirred at room temperature for 1 hour. The reaction mixture was quenched saturated $NH_4Cl$ and extracted by EtOAc. The organic phase was concentrated to afford compound 7c (100 mg, 90%).

Step 3—Synthesis of Compound 7d

To a mixture of compound 7c (50 mg, 0.08 mmol) in toluene (2 mL) at 20° C. was added HCl (0.5 mL) dropwise. The reaction mixture was stirred at room temperature for 20 minutes. The reaction mixture was diluted with water and extracted by EtOAc. The organic phase was purified by $SiO_2$ chromatography, eluting with petroleum ether: ethyl acetate (50/1~5/1) to afford compound 7d (20 mg, 50%).

Step 4—Synthesis of Compound 7e

A mixture of compound 7d (420 mg, 0.73 mmol) and TBAF (511 mg, 1.47 mmol) in THF (30 mL) was stirred at room temperature for 30 minutes. The reaction mixture was washed with 1 N HCl and extracted by EtOAc. The organic phase was concentrated to afford compound 7e (220 mg, 87%).

Step 5—Synthesis of Compound 7f

To the solution of compound 7e (370 mg, 1.0 mmol) and TEA (0.4 mL, 2.5 mmol) in THF (10 ml) was added N,N-bis(trifluoromethanesulfonyl)aniline (768 mg, 2.1 mmol), and stirred at room temperature for 24 hours. The mixture was concentrated in vacuo and purified by $SiO_2$ chromatography, eluting with petroleum ether: ethyl acetate (50/1~5/1) to afford compound 7f (400 mg, 65%).

Step 6—Synthesis of Compound 7g

To a solution of 7f (0.4 g, 0.66 mmol) in 1,4-dioxane was added bis pinacol borate (0.38 g, 1.5 mmol) and $Pd(dppf)Cl_2$ (0.048 g, 0.07 mmol) and KOAc (0.25 g, 4.8 mmol). The reaction mixture was stirred under $N_2$ and heated to 110° C. overnight. After that, the solvent was removed under vacuum, and the residue was purified by $SiO_2$ chromatography, eluting with petroleum ether: ethyl acetate (20/1~5/1) to afford the product 7g (0.33 g, 88%).

Step 7—Synthesis of Compound 7h

A suspension of compound 7g (330 mg, 0.58 mmol), Cap2 (426 mg, 1.28 mmol), $Pd(dppf)_2Cl_2$ (42 mg, 0.058 mmol), $Na_2CO_3$ (0.307 g, 2.9 mmol) and in $THF/H_2O$ (10:1, 20 mL) was refluxed at 95° C. overnight under $N_2$ protection. After that, the mixture was filtered, and the filtrate was washed with water (50 mL) and extracted with EtOAc (100 mL). The organic layer was washed with brine and dried over anhydrous sodium sulfate. After filtration and concentration, the residue was purified by $SiO_2$ chromatography, eluting with DCM: methanol (100/1~50/1) to afford compound 7h (0.2 g, 44%).

Step 8—Synthesis of Compound 7i

To a solution of compound 7h (0.2 g, 0.25 mmol) in 1,4-dioxane (5 mL) was added HCl/1,4-dioxane (2 mL, 3M). Then the mixture was stirred at room temperature for 1 hour. When the reaction completed, the mixture was concentrated in vacuum to afford compound 7i (0.15 g, 99%).

Step 9—Synthesis of Compound 7

To a mixture of compound 7i (150 mg, 0.25 mmol), Cap 1 (96 mg, 0.5 mmol) and HATU (200 mg, 0.5 mmol) in DMF (3 mL) was added DIEA (240 mg, 2 mmol). The resulting mixture was stirred at room temperature for 30 minutes, and LC-MS judged the material was consumed. After filtration, the filtrate was purified by Pre-HPLC to yield compound 7 (130 mg). $^1$H-NMR (MeOD) δ: 7.75-7.78 (m, 2H), 7.43-7.44 (m, 2H), 7.25-7.36 (m, 6H), 7.11-7.18 (m, 3H), 6.47 (s, 1H), 5.52-5.56 (m, 1H), 5.13-5.25 (m, 3H), 4.16-4.19 (m, 2H), 4.05 (s, 2H), 3.79-3.83 (m, 2H), 3.62 (s, 6H), 2.46-2.52 (m, 2H), 1.98-2.23 (m, 8H), 0.82-0.94 (m, 12H). LC/MS: Anal. Calcd. For $[M+H]^+$ $C_{50}H_{56}N_8O_8$: 897.05; found 897.6.

Example 8

Preparation of Compound 18

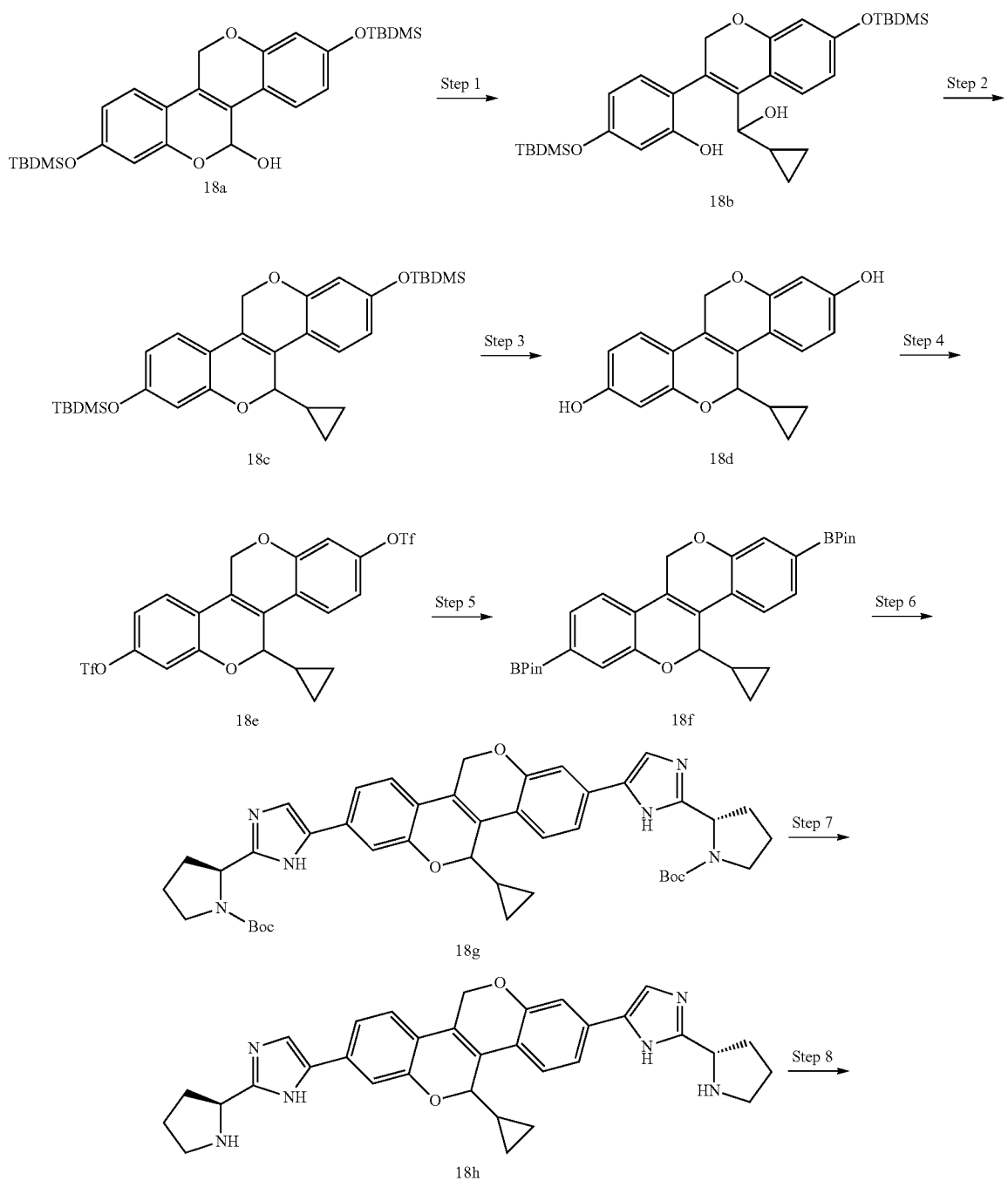

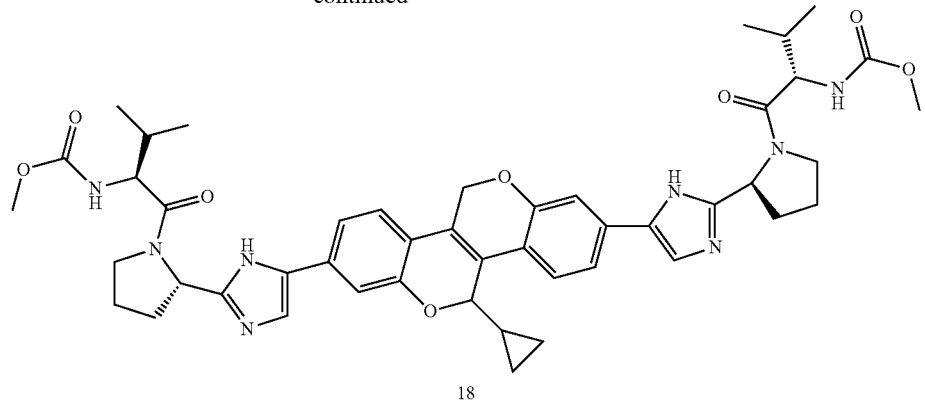

18

Step 1—Synthesis of Compound 18b

Compound 18a was prepared as described in Example 7 (see compound 7b).

To a mixture of compound 18a (200 mg, 0.39 mmol) in THF (10 ml) under a nitrogen atmosphere at 0° C., was added c-PrMgBr (3.9 mL, 2.0 mmol) dropwise. The reaction mixture was stirred at room temperature for 1 hour. The reaction mixture was quenched saturated $NH_4Cl$ and extracted by EtOAc. The organic phase was concentrated to afford compound 18b (200 mg, 92%).

Step 2—Synthesis of Compound 18c

To a mixture of compound 18b (280 mg, 0.50 mmol) in toluene (3 mL) at 20° C., was added HCl (1 mL) dropwise. The reaction mixture was stirred at room temperature for 20 minutes. The reaction mixture was diluted with water and extracted by EtOAc. The organic phase was purified by $SiO_2$ chromatography, eluting with petroleum ether: ethyl acetate (50/1~5/1) to afford compound 18c (180 mg, 66%).

Step 3—Synthesis of Compound 18d

A mixture of compound 18c (2.4 g, 4.4 mmol) and TBAF (3.1 g, 8.9 mmol) in THF (40 mL) was stirred at room temperature for 30 minutes. The reaction mixture was washed with 1 N HCl and extracted by EtOAc. The organic phase was concentrated to afford compound 18d (1.2 g, 92%).

Step 4—Synthesis of Compound 18e

To a solution of compound 18d (1.6 g, 5.2 mmol) and TEA (2.0 mL, 12.0 mmol) in THF (40 ml) was added N,N-bis(trifluoromethanesulfonyl)aniline (3.7 g, 10.4 mmol). The solution was stirred at room temperature for 24 hours. The mixture was concentrated in vacuo and purified by $SiO_2$ chromatography, eluting with petroleum ether: ethyl acetate (50/1~5/1) to afford compound 18e (2.1 g, 72%).

Step 5—Synthesis of Compound 18f

To a solution of 18e (1.1 g, 1.9 mmol) in 20 mL of 1,4-dioxane was added bis pinacol borate (1.1 g, 4.4 mmol) and $Pd(dppf)Cl_2$ (0.14 g, 0.19 mmol) and KOAc (0.75 g, 7.6 mmol). The reaction mixture was stirred under $N_2$ and heated to 110° C. overnight. After that, the solvent was removed under vacuum, and the residue was purified by $SiO_2$ chromatography, eluting with petroleum ether: ethyl acetate (20/1~5/1) to afford the product 18f (0.95 g, 95%).

Step 6—Synthesis of Compound 18g

A suspension of 18f (970 mg, 1.8 mmol), Cap 2 (1.28 g, 4 mmol), $Pd(dppf)_2Cl_2$ (135 mg, 0.18 mmol), $Na_2CO_3$ (0.98 g, 9.2 mmol) and in $THF/H_2O$ (10:1, 50 mL) was refluxed at 95° C. overnight under $N_2$ protection. After that, the mixture was filtered, and the filtrate was washed with water (50 mL) and extracted with EtOAc (100 mL). The organic layer was washed with brine and dried over anhydrous sodium sulfate. After filtration and concentration, the residue was purified by $SiO_2$ chromatography, eluting with DCM: methanol (100/1~50/1) to afford the product compound 18g (0.7 g, 53%).

Step 7—Synthesis of Compound 18h

To a solution of 18g (0.7 g, 0.93 mmol) in 1,4-dioxane (10 mL) was added HCl/1,4-dioxane (5 mL, 3M). Then the mixture was stirred at room temperature for 1 hour. When the reaction completed, the mixture was concentrated in vacuum to give crude compound 18h.

Step 8—Synthesis of Compound 18

To a mixture of compound 18h (550 mg, 0.93 mmol), Cap 1 (384 mg, 2.2 mmol) and HATU (890 mg, 2.2 mmol) in DMF (10 mL) was added DIEA (600 mg, 5 mmol). The resulting mixture was stirred at room temperature for 30 minutes, and LC-MS judged the material was consumed. After filtration, the filtrate was purified by Pre-HPLC followed by SFC separation to afford compound 18 (130 mg).

SFC Separation Conditions:

Column: Chiralcel OJ-H 250×4.6 mm I.D., 5 μm

Solvent: 40% of iso-propanol (0.05% DEA) in $CO_2$

Flow rate: 2.4 mL/min

Wavelength: 340 nm $^1$H-NMR (MeOD) δ: 7.83 (s, 2H), 7.23-7.41 (m, 6H), 5.44-5.48 (m, 1H), 5.19-5.22 (m, 2H), 5.09-5.11 (d, J=8.0 Hz, 1H), 4.97 (s, 1H), 4.20-4.22 (d, J=8.0 Hz, 2H), 3.99 (s, 2H), 3.82-3.88 (m, 2H), 3.64 (s, 6H), 2.51-2.56 (m, 2H), 1.99-2.27 (m, 8H), 1.23-1.28 (m, 1H), 0.87-0.98 (m, 12H), 0.54 (m, 4H). LC/MS: Anal. Calcd. For $[M+H]^+$ $C_{47}H_{56}N_8O_8$: 861.02; found 861.4.

The following compounds of the present invention were made using the methods described in the Example above and substituting the appropriate reactants and/or reagents. The racemic products were then separated into their enantiomers by chiral HPLC. Where the stereochemistry of a particular stereocenter in an isolated enantiomer is unknown, the stereocenter is designated by an "*".

| ID | Structure | Isomer | Parent Wt (P), Observed [M + H]+ (O) |
|---|---|---|---|
| 5 | 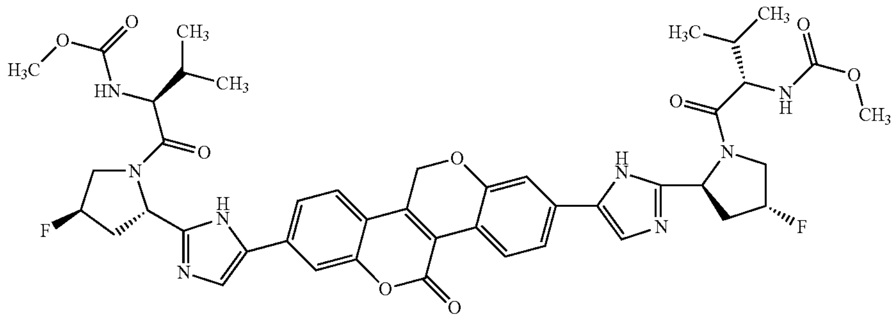 | N/A | P-870.918<br>O-871.6 |
| 6 | 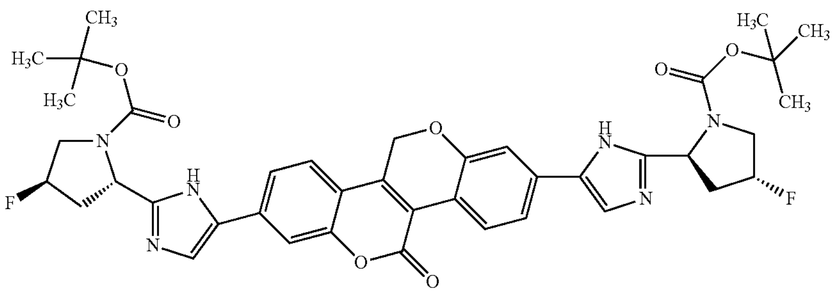 [SMILES: CC(C)(C)OC(=O)N1C[C@H](F)C[C@H]1c1ncc(-c2ccc3c(c2)OCc2c-3c(=O)oc3cc(-c4cnc([C@@H]5C[C@@H](F)CN5C(=O)OC(C)(C)C)[nH]4)ccc23)[nH]1] | N/A | P-756.814<br>O-757.2 |
| 8<br>9 | | Isomer 1<br>Isomer 2 | P-897.053<br>O-897.6<br>O-897.4 |
| 10<br>11<br>12 | | Racemic<br>Isomer 2<br>Isomer 1 | P-927.079<br>O-927.6<br>O-927.4<br>O-927.6 |

-continued
| ID | Structure | Isomer | Parent Wt (P), Observed [M + H]+ (O) |
|---|---|---|---|
| 13 | 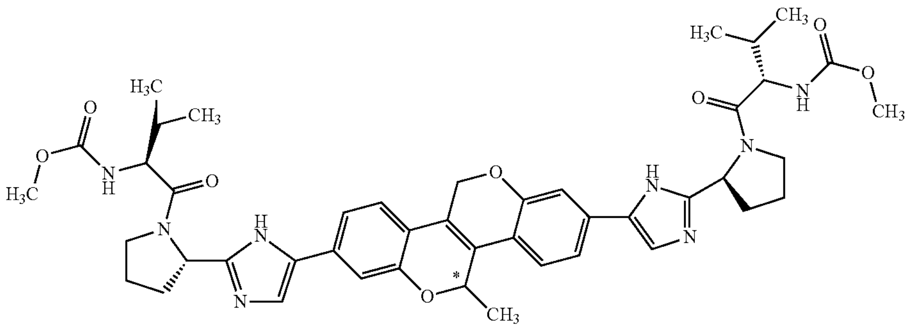 | Racemic | P-834.981 O-835.4 |
| 14 | | Isomer 1 | O-835.2 |
| 15 | | Isomer 2 | O-835.6 |
| 16 | 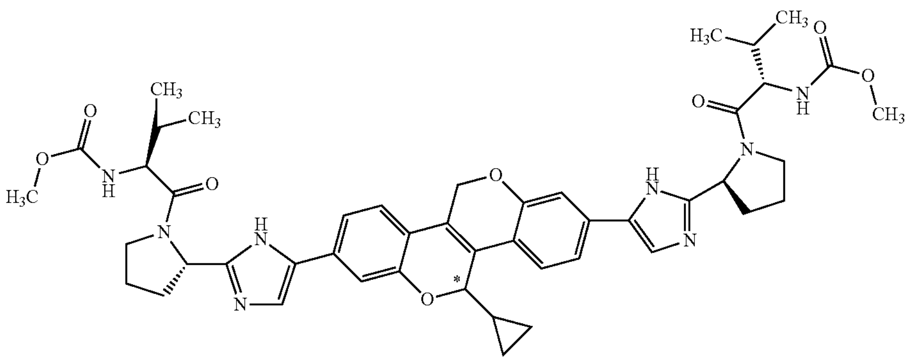 | Isomer 1 | P-861.019 O-861.4 |
| 17 | | Isomer 2 | O-861.6 |
| 18 | | Racemic | O-861.4 |
| 19 | 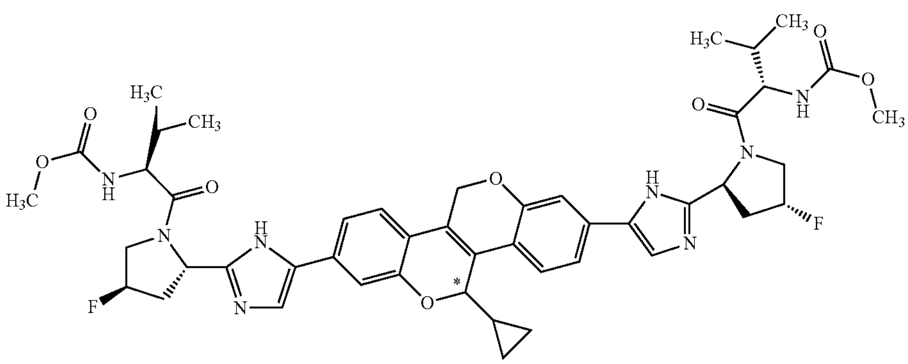 | Racemic | P-897 O-897.4 |
| 20 | | Isomer 1 | O-897.6 |
| 21 | | Isomer 2 | O-897.4 |
Example 9
Preparation of Compound 22
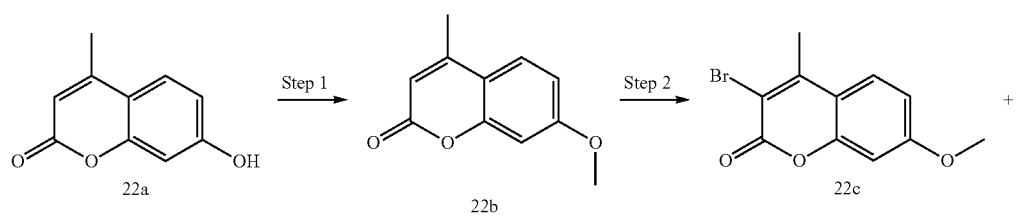

-continued
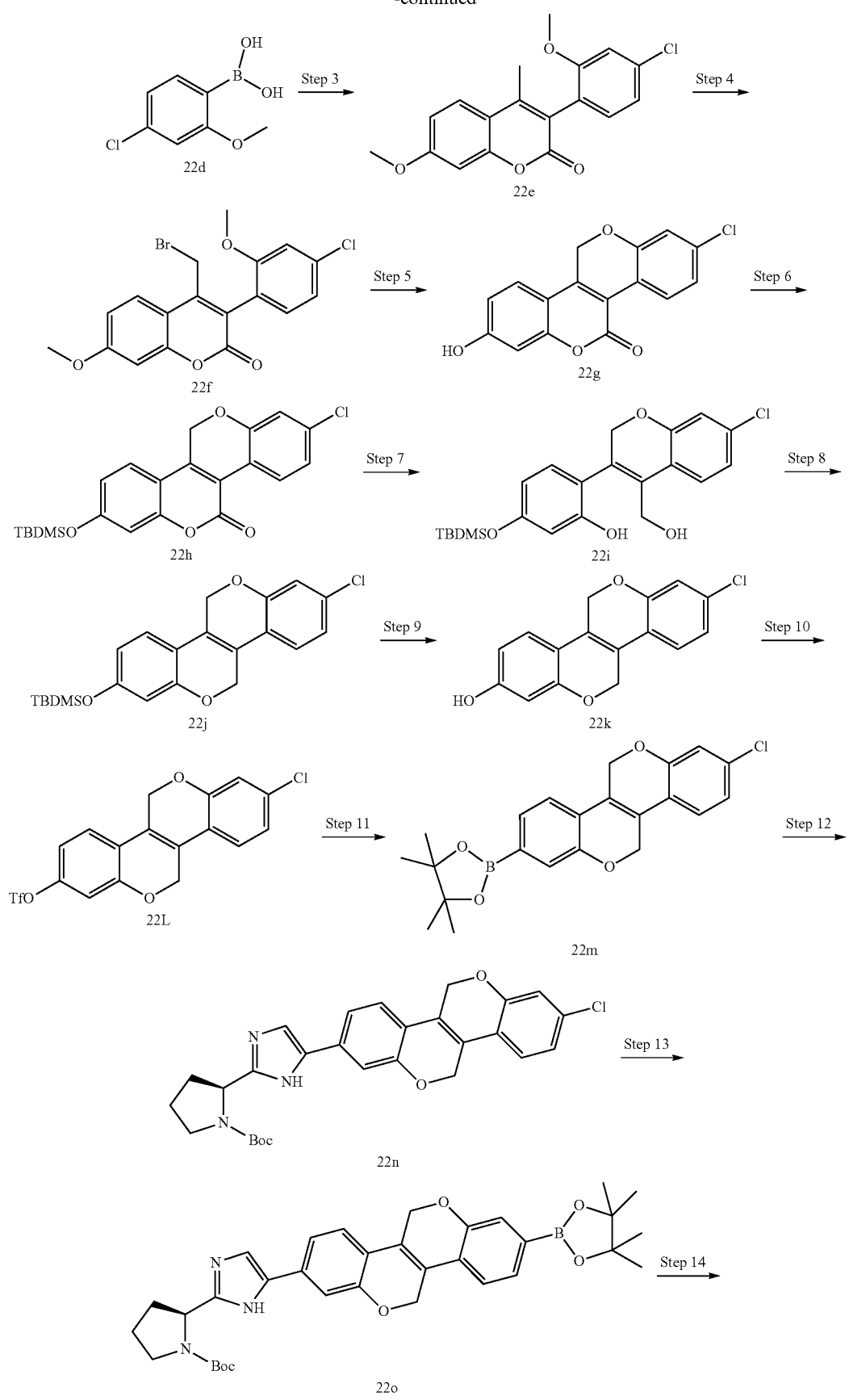

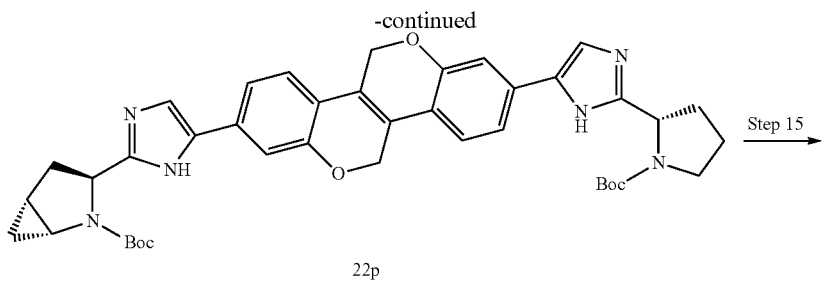

22p

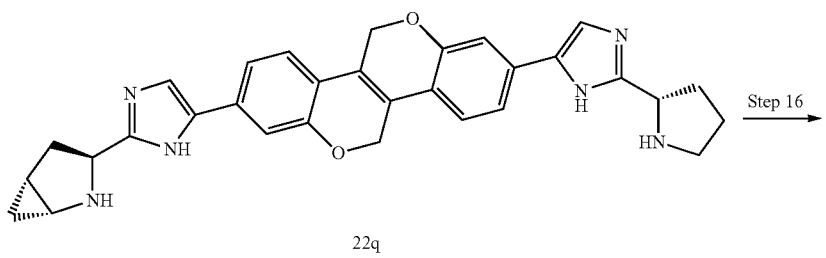

22q

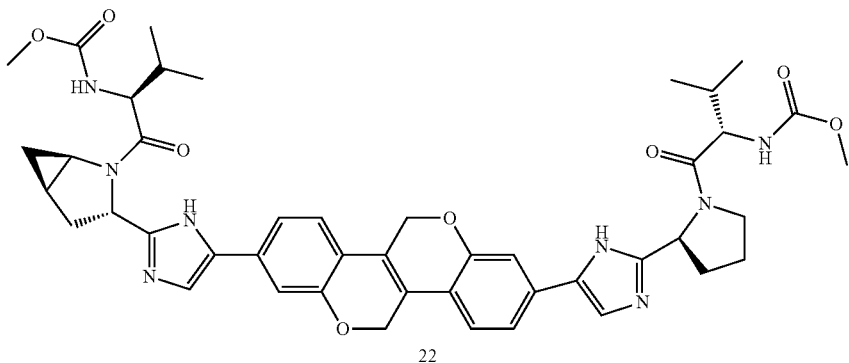

22

Step 1—Synthesis of Compound 22b

To a mixture of compound 22a (5.0 g, 28 mmol) and $K_2CO_3$ (11.7 g, 84 mmol) in DMF (30 mL) was added MeI (5.1 g, 36 mmol) dropwise. The reaction mixture was heated at 20° C. for 2 hours. The reaction mixture was cooled to 0° C., diluted with water, and extracted with EtOAc. The organic phase was concentrated in vacuo to afford compound 22b (5.0 g, 94%).

Step 2—Synthesis of Compound 22c

A mixture of compound 22b (1.0 g, 5.3 mmol), NBS (1.4 g, 7.9 mmol) and BPO (20 mg) in $CHCl_3$ (30 mL) was heated to reflux at 70° C. for 8 hours. The reaction mixture was cooled to 0° C., diluted with water, and extracted with $CHCl_3$. The organic phase was concentrated in vacuo to afford compound 22c (1.0 g, 71%).

Step 3—Synthesis of Compound 22e

A suspension of compound 22c (500 mg, 2.3 mmol), compound 22d (350 mg, 1.8 mmol), $Pd(dppf)_2Cl_2$ (69 mg, 0.09 mmol), and $Na_2CO_3$ (0.6 g, 5.64 mmol) in $THF/H_2O$ (10:1, 20 mL) was refluxed at 95° C. overnight under $N_2$ protection. After that, the mixture was filtered, and the filtrate was washed with water (50 mL) and extracted with EtOAc (100 mL). The organic layer was washed with brine and dried over anhydrous sodium sulfate. After filtration and concentration, the residue was purified by $SiO_2$ chromatography, eluting with petroleum ether: ethyl acetate (100/1~10/1) to afford the compound 22e (0.3 g, 48%).

Step 4—Synthesis of Compound 22f

To a mixture of compound 22e (900 mg, 2.7 mmol) in THF (40 mL) with agitation under a nitrogen atmosphere, was added lithium bis(trimethylsilyl)amide (3.0 mL, 3.0 mmol, 1 M in THF) dropwise at −30° C. The reaction mixture was stirred for 1 hour at −30° C. and then cooled to −76° C. Meantime, the NBS (532 mg, 3.0 mmol) in THF (15 mL) was cooled to −76° C. With fast agitation, the above solution of compound 22e was quickly transferred into NBS/THF solution. The reaction was stirred at −76° C. for 1 hour. The reaction mixture was added saturated solution of $Na_2S_2O_3$, washed with 1 N HCl and extracted with EtOAc. The organic phase was concentrated in vacuo to afford compound 22f (900 mg, 81%).

Step 5—Synthesis of Compound 22g

To a mixture of compound 22f (1.0 g, 2.4 mmol) in $CH_2Cl_2$ (25 mL), was added Boron tribromide (1.3 mL, 8.1 mmol) dropwise at 0° C. The reaction mixture was stirred at room temperature for 24 hours. To the reaction mixture was added saturated $NaHCO_3$ and water, the pH of reaction solution was adjusted to 12 by adding 10 N NaOH, and stirred at room temperature for 2 hours. The organic phase was discarded. The pH of aqueous layer was adjusted to 1 by the addition of concentrated HCl. After filtration, the solid was collected and washed with water to afford compound 22g (500 mg, 69%).

Step 6—Synthesis of Compound 22h

To a mixture of compound 22g (300 mg, 1.0 mmol) and $Et_3N$ (0.2 mL, 1.2 mmol) in THF (10 mL), was added TBDMSCl (180 mg, 1.2 mmol) dropwise. The reaction mixture was stirred at room temperature for 24 hours. The reaction mixture was added saturated $NaHCO_3$ and washed with 1 N HCl. The organic phase was concentrated to afford compound 22h (400 mg, 95%).

Step 7—Synthesis of Compound 22i

To a mixture of $LiAlH_4$ (76 mg, 2.1 mmol) in THF (15 mL) with agitation under a nitrogen atmosphere, was added compound 22h (430 mg, 1.0 mmol) in THF (3 mL) dropwise at 0° C. The reaction mixture was stirred at room temperature for 30 minutes. The reaction mixture was added into saturated $Na_2SO_4$ and extracted by EtOAc. The mixture was concentrated in vacuo to afford compound 22i (400 mg, 93%).

Step 8—Synthesis of Compound 22j

To a mixture of $PPh_3$ (301 mg, 1.1 mmol) in THF (15 mL) with agitation under a nitrogen atmosphere, was added DEAD (200 mg, 1.1 mmol) dropwise at 0° C. The reaction mixture was stirred at room temperature for 30 minutes. Then the mixture was cooled to 0° C. and compound 22i (400 mg, 0.9 mmol) in THF (5 mL) was added dropwise. The reaction mixture was stirred at room temperature for 2 hours. The mixture was concentrated in vacuo and purified by $SiO_2$ chromatography, eluting with petroleum ether: ethyl acetate (30/1~5/1) to afford compound 22j (200 mg, 50%).

Step 9—Synthesis of Compound 22k

A mixture of compound 22j (700 mg, 1.6 mmol) and TBAF (586 mg, 1.6 mmol) in THF (20 mL) was stirred at room temperature for 30 minutes. The reaction mixture was washed with 1 N HCl and extracted by EtOAc. The organic phase was concentrated to afford compound 22k (480 mg, 100%).

Step 10—Synthesis of Compound 22L

To a solution of compound 22k (600 mg, 2.1 mmol) and TEA (254 mg, 2.5 mmol) in DCM (20 mL) was added N,N-bis (trifluoromethanesulfonyl) aniline (824 mg, 2.3 mmol). The mixture was stirred at room temperature for 24 hours. The mixture was concentrated in vacuo and purified by $SiO_2$ chromatography, eluting with petroleum ether: ethyl acetate (50/1~5/1) to afford compound 22L (500 mg, 57%).

Step 11—Synthesis of Compound 22m

To a solution of 22L (500 mg, 1.2 mmol) in 20 mL of 1,4-dioxane was added bis pinacol borate (364 mg, 1.43 mmol) and $Pd(dppf)Cl_2$ (0.044 g, 0.06 mmol) and KOAc (0.234 g, 2.4 mmol). The reaction mixture was stirred under $N_2$ and heated to 110° C. overnight. After that, the solvent was removed under vacuum, and the residue was purified by $SiO_2$ chromatography, eluting with petroleum ether: ethyl acetate (20/1~5/1) to afford the product 22m (300 mg, 63%).

Step 12—Synthesis of Compound 22n

A suspension of compound 22m (300 mg, 0.75 mmol), Cap 2 (263 mg, 0.83 mmol), $Pd(dppf)_2Cl_2$ (30 mg, 0.04 mmol), $Na_2CO_3$ (0.2 g, 1.9 mmol) and in $THF/H_2O$ (10:1, 30 mL) was refluxed at 95° C. overnight under $N_2$ protection. After that, the mixture was filtered, and the filtrate was washed with water and extracted with EtOAc. The organic layer was washed with brine and dried over anhydrous sodium sulfate. After filtration and concentration, the residue was purified by $SiO_2$ chromatography, eluting with DCM: methanol (100/1~30/1) to afford the compound 22n (0.3 g, 78%).

Step 13—Synthesis of Compound 22o

To a solution of compound 22n (300 mg, 0.59 mmol) in 20 mL of 1,4-dioxane was added bis pinacol borate (180 mg, 0.71 mmol), X-phos (28 mg, 0.059 mmol), $Pd_2(dba)_3$ (0.054 g, 0.059 mmol) and KOAc (0.173 g, 1.7 mmol). The reaction mixture was stirred under $N_2$ and heated to 110° C. overnight. After that, the solvent was removed under vacuum, and the residue was purified by $SiO_2$ chromatography, eluting with DCM: methanol (100/1~30/1) to afford the product 22o (300 mg, 85%).

Step 14—Synthesis of Compound 22p

A suspension of compound 22o (300 mg, 0.5 mmol), Cap 3 (180 mg, 0.55 mmol), $Pd(dppf)_2Cl_2$ (18 mg, 0.03 mmol), $Na_2CO_3$ (0.14 g, 1.4 mmol) and in $THF/H_2O$ (10:1, 30 mL) was refluxed at 95° C. overnight under $N_2$ protection. After that, the mixture was filtered, and the filtrate was washed with water and extracted with EtOAc. The organic layer was washed with brine and dried over anhydrous sodium sulfate. After filtration and concentration, the residue was purified by $SiO_2$ chromatography, eluting with DCM: methanol (100/1~10/1) to afford the compound 22p (150 mg, 41%).

Step 15—Synthesis of Compound 22q

To a solution of 22p (150 mg, 0.21 mmol) in 1,4-dioxane (10 mL) was added HCl/1,4-dioxane (5 mL, 3M). Then the mixture was stirred at room temperature for 1 hour. When the reaction completed, the mixture was concentrated in vacuo to yield crude compound 22q.

Step 16—Synthesis of Compound 22

To a mixture of compound 22q (100 mg, 0.2 mmol), Cap 1 (67 mg, 0.4 mmol) and HATU (162 mg, 0.4 mmol) in DMF (3 mL) was added DIEA (120 mg, 2 mmol). The resulting mixture was stirred at room temperature for 30 minutes, and LC-MS judged the material was consumed. After filtration, the filtrate was purified by Pre-HPLC to yield compound 22 (60 mg). $^1H$ NMR (MeOD) δ: 7.81-7.83 (m, 2H), 7.20-7.30 (m, 6H), 5.17-5.21 (m, 4H), 5.04-5.08 (m, 1H), 4.50-4.51 (m, 1H), 4.09-4.21 (m, 2H), 3.78-3.86 (m, 2H), 3.64-3.69 (s, 6H), 2.38-2.67 (m, 3H), 2.00-2.31 (m, 6H), 1.05-1.07 (m, 1H), 0.90-0.99 (m, 14H). LC/MS: Anal. Calcd. For $[M+H]^+$ $C_{45}H_{52}N_8O_8$: 832.97; found 833.4.

Example 10

Cell-Based HCV Replicon Assay

To measure cell-based anti-HCV activity of selected compounds of the present invention two complimentary assays were employed. In the first assay, replicon cells were seeded at 2000 cells/well in 384-well flat bottom tissue culture treated clear bottom plate (Corning 3707) in the presence of the test compound. Various concentrations of test compound, typically in 10 serial dilutions, were added to the assay mixture, with the starting concentration ranging from 333.3 nM to 1.667 nM. The final concentration of DMSO was 0.5%. Fetal bovine serum was 5%, in the assay media. Cells were harvested on day 3 by removing media and washing the cells with a suitable wash buffer. The cells were lysed with the addition of 1× Qiagen lysis buffer (Cat #1062731). The replicon RNA level was measured using real time PCR (TaqMan® EZ RT-PCR, Applied Biosystems 403028) with the following primers and probes:

```
Neo Forward:
                                            (SEQ ID NO: 1)
CCG GCT ACC TGC CCA TTC Neo Reverse:
                                            (SEQ ID NO: 2)
CCA GAT CAT CCT GAT CGA CAA G Neo Probe:
                                            (SEQ ID NO: 3)
FAM-ACA TCG CAT CGA GCG AGC ACG TAC-Tamra Cyc probe:
                                            (SEQ ID NO: 4)
5'-JOE-CGCGTCTCCTTTGAGCTGTTTGCA-Tamra-3'

Cyc Forward Primer:
                                            (SEQ ID NO: 5)
ACGGCGAGCCCTTGG Cyc Reverse Primer:
                                            (SEQ ID NO: 6)
TTTCTGCTGTCTTTGGGACCT
```

Cyclophilin RNA was used as endogenous control and was amplified in the same reaction as NS5B (multiplex PCR). The real-time RT-PCR reactions were run on ABI PRISM 7900HT Sequence Detection System using the following program: 50° C. for 2 minutes, 60° C. for 30 minutes, 95° C. for 5 minutes, 40 cycles of 94° C. for 20 sec, 55° C. for 1 minute.

The amount of HCV replicon RNA per cell is quantified using a linear regression curve for a known nanogram (ng) amount of HCV replicon total RNA. This is established by plotting the Cycle Threshold values (Ct) from the Neo probe and primer set versus the log (ng) for each HCV replicon total RNA standard. The amount of HCV RNA for each replicon sample is calculated by taking the sample's Ct value, minus the line intercept, divided by the slope of the line. Similarly, the amount of Cyclophilin mRNA per cell is also quantified using a linear regression curve for a known nanogram (ng) amount of HCV replicon total RNA. Again, this is established by plotting the Cycle Threshold values (Ct) from the Cyclophilin probe and primer set versus the log (ng) for each HCV replicon total RNA standard.

In the alternate assay, 1000 cells were seeded per well in a 384-well collagen coated black plate from Greiner bio-one (Cat #781946) in 5% FBS. Inhibitors of this invention were added at 24 hours post-seeding, and the plates were incubated for 3 days. Cells were subsequently lysed with Qiagen lysis buffer (Cat #1062731) to extract the RNA. HCV replicon RNA level was measured by real-time PCR using the RNA-to-CT kit from Applied Biosystem (Cat #4392656) and genotype-specific primers and probes. The amplicon was located within NS5B. The sequence of the PCR primers were as follows: 5B.2F, ATGGACAGGCGCCCTGA (SEQ. ID NO. 7); 5B.2R, TTGATGGGCAGCTTGGTTTC (SEQ. ID NO. 8); the probe sequence was FAM-labeled CACGC-CATGCGCTGCGG (SEQ. ID NO. 9). To detect genotype 1A the primer 1A F, TGCGGAACCGGTGAGTACA (SEQ ID NO:10) and 1A R, GCGGGTTTATCCAAGAAAGGA (SEQ ID NO: 11) were used; the probe sequence was FAM-CGGAATTGCCAGGACGACCGG (SEQ ID NO:12).

The real-time RT-PCR reactions were run on ABI PRISM 7900HT or Viia7 Sequence Detection System using the following program: 48° C. for 30 minutes, 95° C. for 10 minutes, 40 cycles of 95° C. for 15 sec, 60° C. for 1 minute. The 50% effective concentration ($EC_{50}$) was the drug concentration necessary to achieve an increase in the cycle threshold ($C_T$) of 1 over the projected baseline $C_T$. The $EC_{90}$ was the drug concentration necessary to achieve an increase in $C_T$ of 3.2 over the projected baseline $C_T$.

Data was obtained for various compounds of the present invention using the methods described in the Example above, and is presented in the table immediately below, along

| Compound ID | 1A IC50 (nM) | 1A Y93H IC50 (nM) | 1B IC50 (nM) | 2B IC50 (nM) | 3A IC50 (nM) |
|---|---|---|---|---|---|
| 1 | 0.0050 | 7.361 | 0.0054 | 12.13 | 1 |
| 2 | 200 | 2000 | | | |
| 3 | 0.0056 | 24.46 | 0.0063 | 4.204 | 0.451 |
| 4 | 200 | 2000 | | | |
| 5 | 0.0153 | 0.337 | 0.0044 | 100 | 1 |
| 6 | 975.1 | 3081 | | | |
| 7 | 0.0076 | 4.292 | 0.002 | 1.004 | 0.062 |
| 8 | 0.0337 | 20.4 | 0.021 | 6.648 | 0.969 |
| 9 | 0.0099 | 3.944 | 0.0073 | 1.904 | 0.172 |
| 10 | 0.0035 | 2.943 | | 2.719 | 0.233 |
| 11 | 0.010 | | 0.006 | | |
| 12 | 0.0251 | 2.444 | | | 1.817 |
| 13 | 0.0344 | 23.83 | | 11.97 | 1 |
| 14 | 0.0122 | 31.8 | | 24.54 | |
| 15 | 0.0229 | 126.7 | | 15.3 | |
| 16 | 0.0118 | 6.309 | | 0.6208 | 3.743 |
| 17 | 0.0115 | 57.91 | | | |
| 18 | 0.0081 | 14.32 | | | |
| 19 | 0.0192 | 2.309 | | | |
| 20 | 0.0866 | 1.965 | | | |
| 21 | 0.0156 | 2.166 | | | |
| 22 | 0.0023 | 2.009 | | 15.98 | 2.023 |

NOTE:
Blank entries denote that data was not available.

What is claimed is:

1. A compound of formula (I):

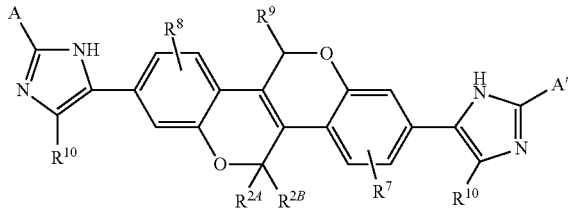

(I)

or a pharmaceutically acceptable salt thereof, wherein:

A is:

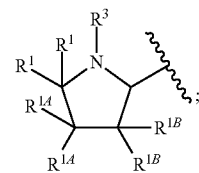

A' is:

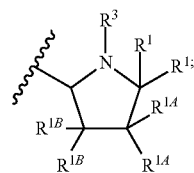

each occurrence of $R^1$ is independently selected from H, $C_1$-$C_6$ alkyl, $C_1$-$C_6$ haloalkyl and halo;

each occurrence of $R^{1A}$ is independently selected from H, $C_1$-$C_6$ alkyl, $C_1$-$C_6$ haloalkyl and halo, or one $R^{1A}$ group and an $R^1$ group that are attached to same ring, together with the ring carbon atoms to which they are attached, can combine to form a fused $C_3$-$C_7$ cycloalkyl group, or two $R^{1A}$ groups that are attached to the same carbon atom, and the common carbon atom to which they are attached, can combine to form a spirocyclic $C_3$-$C_7$ cycloalkyl group;

each occurrence of $R^{1B}$ is independently H, $C_1$-$C_6$ alkyl, $C_1$-$C_6$ haloalkyl or halo, or an $R^{1B}$ group and an $R^{1A}$ group that are attached to the same ring, together with the carbon atoms to which they are attached, can combine to form a fused $C_3$-$C_7$ cycloalkyl group, or an $R^{1B}$ group and an $R^1$ group that are attached to the same ring, can combine to form a bridging group of the formula —$CH_2$— or —$CH_2CH_2$—;

$R^{2A}$ is H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, 6 to 10-membered bicyclic heterocycloalkyl, $C_6$-$C_{10}$ aryl, or —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said 6 to 10-membered bicyclic heterocycloalkyl, or said $C_6$-$C_{10}$ aryl group, can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);

$R^{2B}$ is H; or alternatively, $R^{2A}$ and $R^{2B}$, together with the common carbon atom to which they are attached, form a carbonyl group;

each occurrence of $R^3$ is independently —C(O)—C(R$^4$)$_2$NHC(O)O—R$^5$, —C(O)O—R$^5$; or —C(O)—C(R$^4$)$_2$NR$^{11}$R$^{12}$;

each occurrence of $R^4$ is independently selected from H, $C_1$-$C_6$ alkyl, $C_1$-$C_6$ haloalkyl, $C_6$-$C_{10}$ aryl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group, said $C_6$-$C_{10}$ aryl group and said $C_3$-$C_7$ cycloalkyl group can be optionally substituted with up to 5 groups, each independently selected from halo, —CN, $C_1$-$C_6$ alkyl, $C_1$-$C_6$ haloalkyl, $C_3$-$C_7$ cycloalkyl, —O—$C_1$-$C_6$ alkyl, —N(R$^6$)$_2$ and —O—($C_1$-$C_6$ haloalkyl), and wherein said $C_3$-$C_7$ cycloalkyl group can be optionally fused to a 4 to 6-membered monocyclic heterocycloalkyl group, and wherein said 4 to 8-membered monocyclic heterocycloalkyl group and said $C_3$-$C_7$ cycloalkyl group can be substituted on a ring carbon atom with a spirocyclic $C_3$-$C_6$ cycloalkyl group; and wherein said $C_3$-$C_7$ cycloalkyl group can be substituted on a ring carbon atom with a spirocyclic 3 to 6-membered monocyclic heterocycloalkyl group, and wherein two $R^4$ groups, that are attached to a common carbon atom, together with the common carbon atom to which they are attached, can join to form a $C_3$-$C_7$ cycloalkyl group;

each occurrence of $R^5$ is independently selected from $C_1$-$C_6$ alkyl, $C_3$-$C_7$ cycloalkyl and $C_6$-$C_{10}$ aryl;

each occurrence of $R^6$ is independently selected from H, $C_1$-$C_6$ alkyl and $C_3$-$C_7$ cycloalkyl;

$R^7$ and $R^8$ each represent up to 2 substituents, each independently selected from H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, $C_6$-$C_{10}$ aryl, phenyl and —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said $C_6$-$C_{10}$ aryl group, or said phenyl group can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);

$R^9$ is H, $C_1$-$C_6$ alkyl, $C_3$-$C_7$ cycloalkyl, phenyl or halo;

each occurrence of $R^{10}$ is independently H, $C_1$-$C_6$ alkyl, $C_3$-$C_7$ cycloalkyl, phenyl or halo;

each occurrence of $R^{11}$ is independently $C_1$-$C_6$ alkyl, $C_1$-$C_6$ haloalkyl, $C_3$-$C_7$ cycloalkyl, or phenyl; and each occurrence of $R^{12}$ is independently $C_1$-$C_6$ alkyl, $C_1$-$C_6$ haloalkyl, $C_3$-$C_7$ cycloalkyl, or phenyl.

2. The compound according to claim 1, or pharmaceutically acceptable salt thereof, wherein $R^{2A}$ and $R^{2B}$, together with the common carbon atom to which they are attached, form a carbonyl group.

3. The compound according to claim 1, or pharmaceutically acceptable salt thereof, wherein, $R^{2A}$ is H, $C_1$-$C_6$ alkyl, $C_3$-$C_7$ cycloalkyl, thiazole, thiophene, or phenyl, wherein said $C_3$-$C_7$ cycloalkyl group, said thiophene group or said phenyl group can be optionally substituted with up to 3 groups, and said thiazole group can be optionally substituted with up to 2 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl); and $R^{2B}$ is H.

4. The compound according to claim 1, or pharmaceutically acceptable salt thereof, wherein A and A' are each independently selected from:

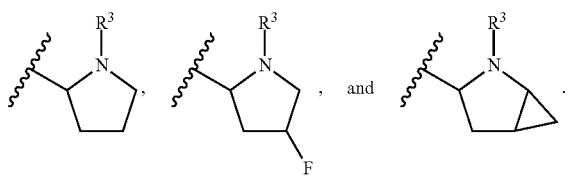

5. The compound according to claim 4, or pharmaceutically acceptable salt thereof, wherein each occurrence of $R^3$ is independently —C(O)—C(R$^4$)$_2$NHC(O)O—R$^5$.

6. The compound according to claim 4, or pharmaceutically acceptable salt thereof, wherein each occurrence of $R^3$ is independently —C(O)O—R$^5$.

7. The compound of claim 1 of the formula:

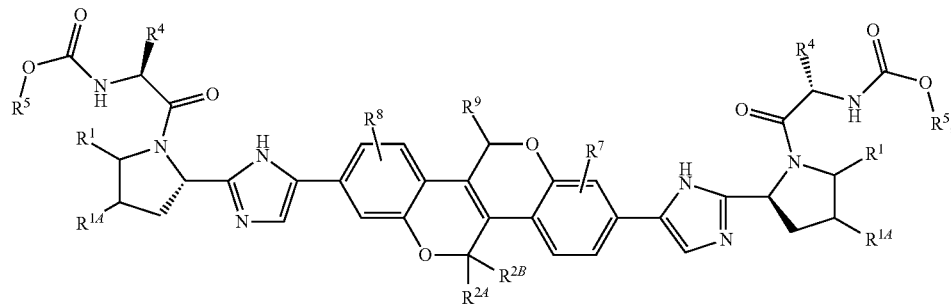

(IA)

or a pharmaceutically acceptable salt thereof,
wherein:
$R^{2A}$ is H, $C_1$-$C_6$ alkyl, $C_3$-$C_7$ cycloalkyl, phenyl, thiophene, or thiazole, wherein said $C_3$-$C_7$ cycloalkyl group, said thiophene group, or said phenyl group can be optionally substituted with up to 3 groups, and said thiazole group can be optionally substituted with up to 2 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl); and
$R^{2B}$ is H;
or alternatively, $R^{2A}$ and $R^{2B}$, together with the common carbon atom to which they are attached, form a carbonyl group;
$R^7$ and $R^8$ are as defined in claim 1,
each occurrence of $R^9$ and $R^{10}$ are independently H, F, Cl, $CH_3$, or isopropyl;
each occurrence of $R^4$ is independently $C_1$-$C_6$ alkyl;
each occurrence of $R^5$ is independently $C_1$-$C_6$ alkyl;
$R^1$ is H, and
each occurrence of $R^{1A}$ is independently selected from H or F.

8. The compound of claim 7, or pharmaceutically acceptable salt thereof, wherein at least one occurrence of $R^4$ is isopropyl.

9. The compound of claim 7, or pharmaceutically acceptable salt thereof, wherein at least one occurrence of $R^5$ is methyl.

10. The compound of claim 9, or pharmaceutically acceptable salt thereof, wherein $R^{2A}$ is H; methyl, cyclopropyl, or phenyl, wherein said phenyl group can be optionally substituted with —O—$C_1$-$C_6$ alkyl.

11. The compound of claim 9, or pharmaceutically acceptable salt thereof, wherein $R^{2A}$ and $R^{2B}$, together with the common carbon atom to which they are attached, form a carbonyl group.

12. The compound of claim 1 of the structure:

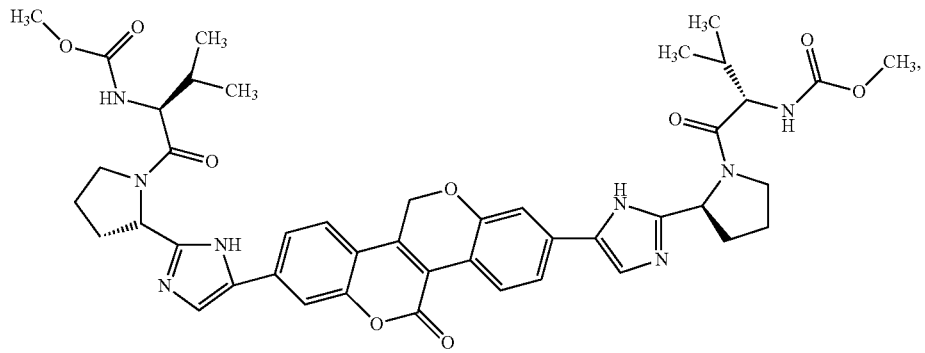

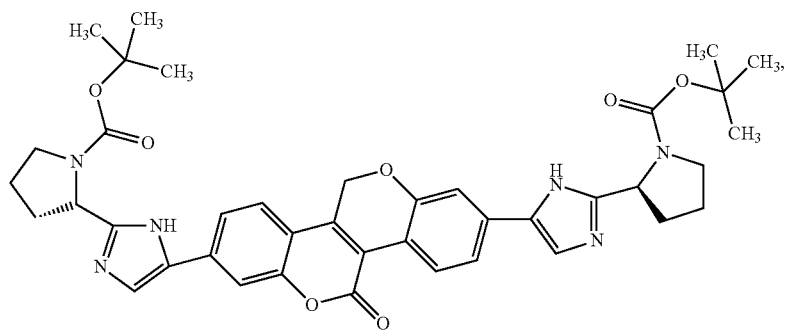

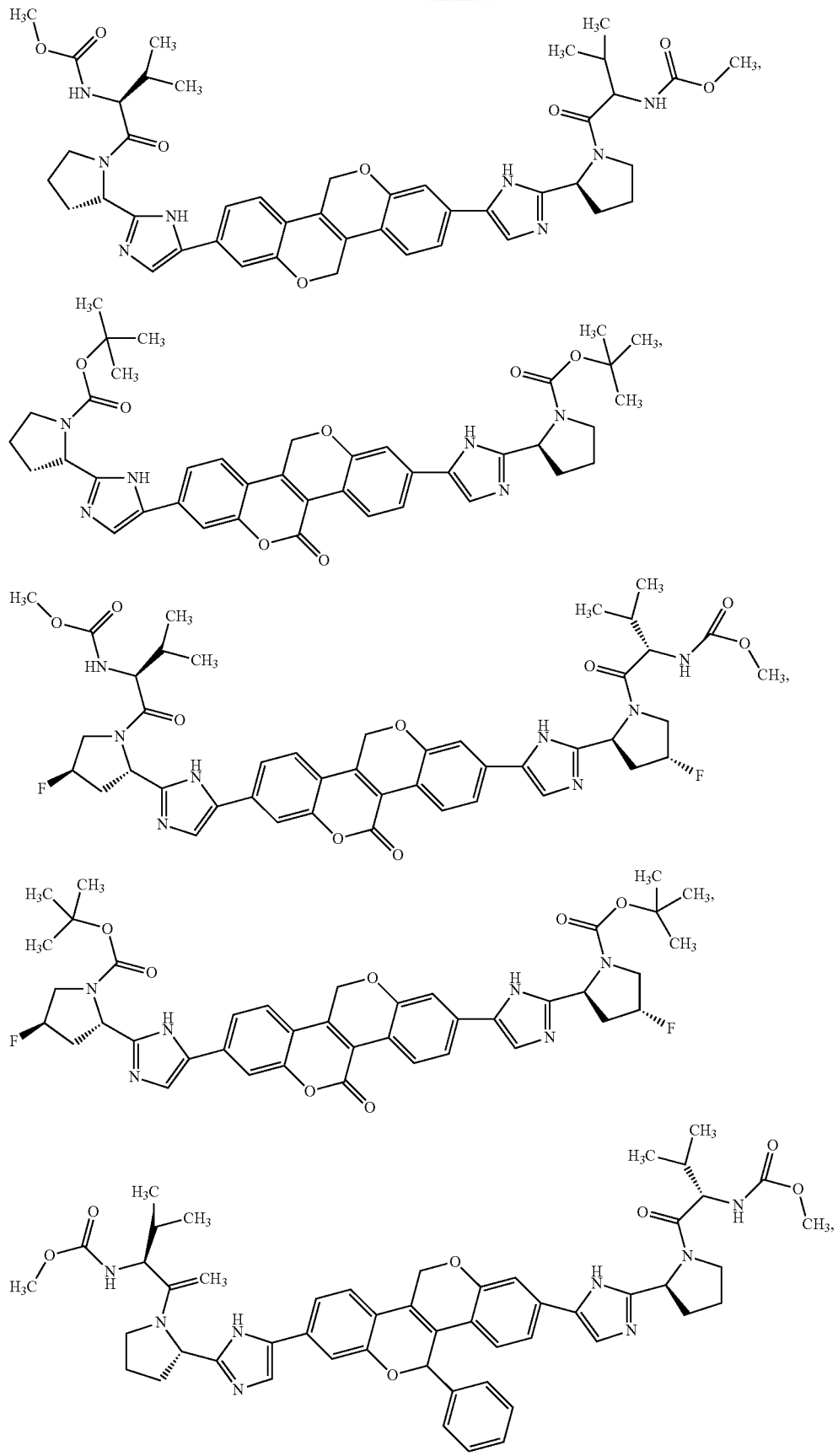

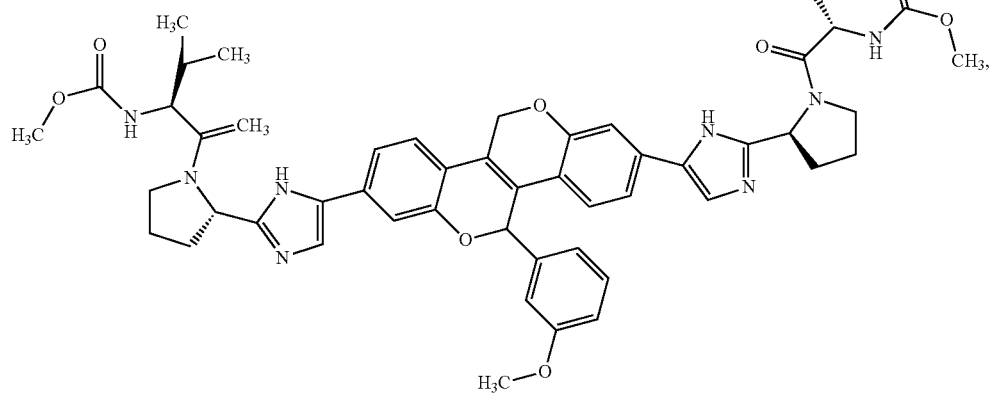
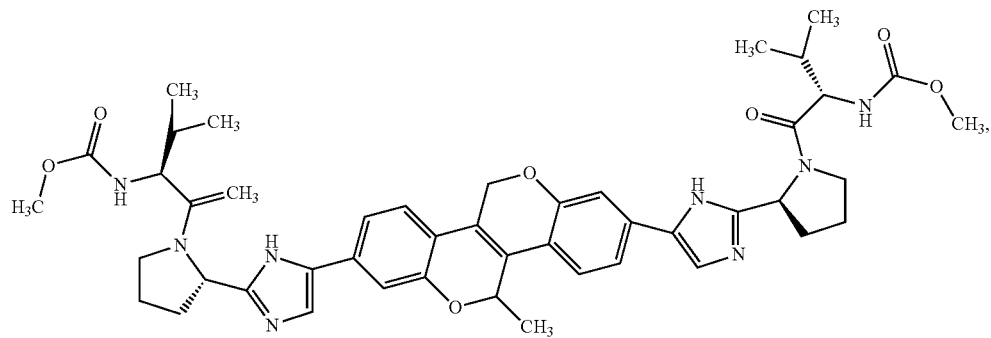
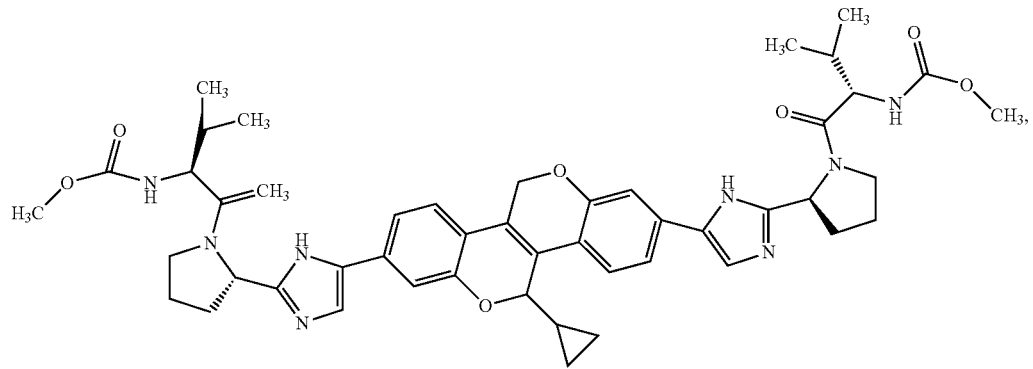
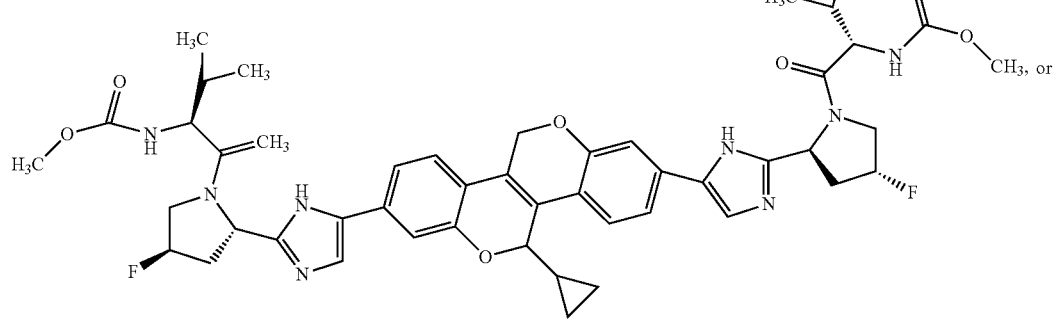

-continued

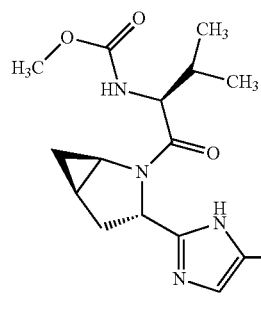 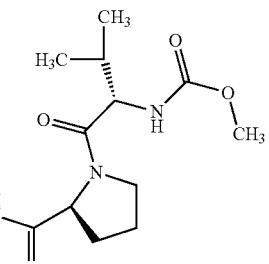

or a pharmaceutically acceptable salt thereof.

13. A pharmaceutical composition comprising an effective amount of the compound of claim 1, or pharmaceutically acceptable salt thereof and a pharmaceutically acceptable carrier.

14. The pharmaceutical composition according to claim 13 further comprising a second therapeutic agent selected from the group consisting of HCV antiviral agents, immunomodulators, and anti-infective agents.

15. The pharmaceutical composition according to claim 14, further comprising a third therapeutic agent selected from the group consisting of HCV protease inhibitors, HCV NS5A inhibitors and HCV NS5B polymerase inhibitors.

16. A method of treating a patient infected with HCV comprising the step of administering an amount of the compound according to claim 1, or a pharmaceutically acceptable salt thereof, in an amount effective to treat infection by HCV in said patient.

17. The method according to claim 16, further comprising the step of administering an HCV protease inhibitor to said patient.

18. The method according to claim 16, further comprising the step of administering ribavirin to said patient.

19. The method according to claim 16, further comprising the step of administering from one to three additional therapeutic agents to said patient, wherein the additional therapeutic agents are each independently selected from HCV protease inhibitors, HCV NS5A inhibitors and HCV NS5B polymerase inhibitors.

20. The method according to claim 19, wherein the one to three additional therapeutic agents comprises MK-5172.

21. The method according to claim 19, wherein the one to three additional therapeutic agents comprises Sofosbuvir.

* * * * *